United States Patent
Kosaka et al.

(10) Patent No.: US 12,014,826 B2
(45) Date of Patent: Jun. 18, 2024

(54) KNOWLEDGE GENERATION SYSTEM, METHOD, AND PROGRAM

(71) Applicant: NEC Corporation, Tokyo (JP)

(72) Inventors: Yuki Kosaka, Tokyo (JP); Masahiro Kubo, Tokyo (JP)

(73) Assignee: NEC CORPORATION, Tokyo (JP)

(*) Notice: Subject to any disclaimer, the term of this patent is extended or adjusted under 35 U.S.C. 154(b) by 482 days.

(21) Appl. No.: 17/284,612

(22) PCT Filed: Oct. 25, 2018

(86) PCT No.: PCT/JP2018/039692
§ 371 (c)(1),
(2) Date: Apr. 12, 2021

(87) PCT Pub. No.: WO2020/084734
PCT Pub. Date: Apr. 30, 2020

(65) Prior Publication Data
US 2021/0343413 A1    Nov. 4, 2021

(51) Int. Cl.
*G16H 50/20* (2018.01)
*G06F 40/166* (2020.01)
(Continued)

(52) U.S. Cl.
CPC ........... *G16H 50/20* (2018.01); *G06F 40/166* (2020.01); *G06F 40/289* (2020.01); *G06F 40/40* (2020.01)

(58) Field of Classification Search
CPC ........ G16H 50/20; G16H 40/60; G16H 50/70; G16H 70/20; G06F 40/166; G06F 40/289; G06F 40/40; G06F 40/30; G06Q 10/10
See application file for complete search history.

(56) References Cited

U.S. PATENT DOCUMENTS

2014/0372522 A1* 12/2014 Orona ............... G16H 40/63
                                                    709/204
2015/0154367 A1   6/2015 Shetty et al.
(Continued)

FOREIGN PATENT DOCUMENTS

JP    2004206571 A    7/2004
JP    2006079469 A    3/2006
(Continued)

OTHER PUBLICATIONS

International Search Report of PCT Application No. PCT/JP2018/039692 dated Jan. 22, 2019.
(Continued)

*Primary Examiner* — Robert W Morgan
*Assistant Examiner* — Liza Tony Kanaan

(57) ABSTRACT

A sentence extraction means extracts a sentence that is different from a cause or a coping method included in knowledge corresponding to a predetermined event and is related to the predetermined event, from an unconfirmed work record. A group selection means selects a group based on a similarity between a first character string of the extracted sentence that is likely to represent a cause or a coping method and a group generated in advance. A character string selection means selects a second character string from the group, and a replacement means replaces the first character string in the work record with the second character string. When a predetermined condition is satisfied, a knowledge generation means selects a character string from the group and generates new knowledge based on the character string.

7 Claims, 12 Drawing Sheets

(51) Int. Cl.
    *G06F 40/289*     (2020.01)
    *G06F 40/40*     (2020.01)

(56) References Cited

U.S. PATENT DOCUMENTS

| | | | | |
|---|---|---|---|---|
| 2016/0148105 A1* | 5/2016 | Henmi | .................. | G06F 3/0484 |
| | | | | 706/11 |
| 2018/0218127 A1* | 8/2018 | Salazar | .................. | G16H 50/30 |

FOREIGN PATENT DOCUMENTS

| | | | |
|---|---|---|---|
| JP | 2007108814 A | | 4/2007 |
| JP | 2016099967 A | | 5/2016 |
| JP | 2017504103 A | | 2/2017 |
| JP | 2017-107261 A1 | | 6/2017 |
| JP | 2017111756 A | | 6/2017 |

OTHER PUBLICATIONS

Japanese Office Action for JP Application No. 2020-552449 dated May 24, 2022 with English Translation.

* cited by examiner

FIG. 3

SENTENCE 1: PERFORM SPUTUM SUCTION DUE TO SAT DECREASE

SENTENCE 2: SAT DECREASED TO 90%, SPUTUM WAS SUCTIONED BECAUSE BREATHING WAS DIFFICULT DUE TO ACCUMULATED SPUTUM

| INSTANCE | DISTANCE | LENGTH | SUM OF DISTANCE AND LENGTH |
|---|---|---|---|
| INSTANCE α | 0.9 | 1.0 | 1.0 |
| INSTANCE β | 0.2 | 0.2 | 0.4 |
| INSTANCE γ | 1.0 | 0.3 | 1.3 |

KNOWLEDGE GENERATION SYSTEM, METHOD, AND PROGRAM

This application is a National Stage Entry of PCT/JP2018/039692 filed on Oct. 25, 2018, the contents of all of which are incorporated herein by reference, in their entirety.

TECHNICAL FIELD

The present invention relates to a knowledge generation system, a knowledge generation method, and a knowledge generation program for generating knowledge which is information representing a cause or coping method corresponding to an event occurring in work.

BACKGROUND ART

Patient assessment is to identify causes or coping methods corresponding events occurring in work of nurses. The patient assessment is one of the most important work of nurses. Proper nursing is not provided unless nurses accurately and quickly perform the patient assessment without omissions. Note that, in this case, examples of the event include "saturation (SAT) decrease", "blood pressure decrease", "pulse decrease" and the like. Here, "SAT" means blood oxygen concentration.

Note that PTL 1 describes a computer device which monitors patient information representing a clinical condition based on a clinical protocol that includes patient-care instructions that must be completed within a time period, and provides the patient-care instructions to the user based on a result of the monitoring.

In addition, PTL 2 describes a system that efficiently narrows down variances that have an important effect on improving the quality of medical care and assists extraction of medical practices which are causes of the variances. In the invention described in PTL 2, the variance is a difference between a standard medical care plan and actual medical care.

CITATION LIST

Patent Literature

PTL 1: Japanese Patent Application Laid-Open No. 2017-504103
PTL 2: Japanese Patent Application Laid-Open No. 2007-108814

SUMMARY OF INVENTION

Technical Problem

An experienced nurse can perform patient assessment, but the patient assessment is difficult for a new nurse. The experienced nurse, for example, uses experience-based knowledge to perform the patient assessment. In addition, the experienced nurse determines a cause or a coping method for an event occurring in a patient on the spot according to the patient's condition, and proceed with the coping promptly. However, there is no room for documentation of information (hereinafter referred to as knowledge) representing the cause or coping method corresponding to the event because there are many variations of the cause or coping method corresponding to the event. Therefore, it is difficult to comprehensively document knowledge. As a result, it is difficult for the new nurse to inherit sufficient knowledge from the experienced nurse, which makes the patient assessment difficult for the new nurse.

In addition, documentation by asking the experienced nurse for knowledge is conceivable in order to deliver the knowledge to a newcomer, but such a method causes a lot of new work load on the veteran nurse and the like, which is not preferable. In addition, it is also conceivable that the newcomer works with the experienced nurse and the newcomer remembers knowledge in the process of working with the experienced nurse. However, it is difficult for the newcomer to remember sufficient knowledge because a period during which the newcomer and the experienced nurse can work together is limited.

Therefore, it is preferable that knowledge can be generated in the process of carrying out normal work. This applies not only to the nurse work but also to various types of other work (for example, work in a factory or the like).

Therefore, an object of the present invention is to provide a knowledge generation system, a knowledge generation method, and a knowledge generation program capable of newly generating knowledge in a process of performing normal work by a worker.

Solution to Problem

A knowledge generation system according to the present invention includes: a knowledge storage means for storing knowledge which is information representing a cause or coping method corresponding to an event; a sentence extraction means for extracting a sentence which is different from a cause or a coping method included in knowledge corresponding to a predetermined event and is related to the predetermined event from an unconfirmed work record; a group selection means for selecting any one group including a plurality of character strings among groups of character strings, obtained by grouping the character strings which are likely to represent the cause or coping method corresponding to the event and are obtained from a past work record, based on a similarity between each of the groups including the plurality of character strings and a first character string of the extracted sentence that is likely to represent the cause or coping method; a character string selection means for selecting a character string included in the selected group including the plurality of character strings as a second character string; a replacement means for replacing the first character string in the work record with the second character string selected by the character string selection means; and a knowledge generation means for generating new knowledge based on any of the character strings included in the group when a predetermined condition regarding a confirmation status of the work record in which the first character string has been replaced with the second character string is satisfied.

A knowledge generation method according to the present invention causes a computer including a knowledge storage means for storing knowledge which is information representing a cause or coping method corresponding to an event, to execute: a sentence extraction process of extracting a sentence which is different from a cause or a coping method included in knowledge corresponding to a predetermined event and is related to the predetermined event from an unconfirmed work record; a group selection process of selecting any one group including a plurality of character strings among groups of character strings, obtained by grouping the character strings which are likely to represent the cause or coping method corresponding to the event and are obtained from a past work record, based on a similarity between each of the groups including the plurality of character strings and a first character string of the extracted sentence that is likely to represent the cause or coping method; a character string selection process of selecting a character string included in the selected group including the plurality of character strings as a second character string; a replacement process of replacing the first character string in the work record with the second character string selected in the character string selection process; and a knowledge generation process of generating new knowledge based on any of the character strings included in the group when a predetermined condition regarding a confirmation status of the work record in which the first character string has been replaced with the second character string is satisfied.

A knowledge generation program according to the present invention, installed in a computer including a knowledge storage means for storing knowledge which is information representing a cause or coping method corresponding to an event, causes the computer to execute: a sentence extraction process of extracting a sentence which is different from a cause or a coping method included in knowledge corresponding to a predetermined event and is related to the predetermined event from an unconfirmed work record; a group selection process of selecting any one group including a plurality of character strings among groups of character strings, obtained by grouping the character strings which are likely to represent the cause or coping method corresponding to the event and are obtained from a past work record, based on a similarity between each of the groups including the plurality of character strings and a first character string of the extracted sentence that is likely to represent the cause or coping method; a character string selection process of selecting a character string included in the selected group including the plurality of character strings as a second character string; a replacement process of replacing the first character string in the work record with the second character string selected in the character string selection process; and a knowledge generation process of generating new knowledge based on any of the character strings included in the group when a predetermined condition regarding a confirmation status of the work record in which the first character string has been replaced with the second character string is satisfied.

Advantageous Effects of Invention

According to the present invention, the knowledge can be newly generated in the process of performing the normal work by the worker.

BRIEF DESCRIPTION OF DRAWINGS

FIG. 3 It depicts an explanatory view illustrating an example of a sentence extracted by a pre-processing sentence extraction unit.

DESCRIPTION OF EMBODIMENTS

Hereinafter, an exemplary embodiment of the present invention will be described with reference to the accompanying drawings. Note that a "sentence" in the following exemplary embodiment may be a description other than the sentence. Similarly, a "character string" in the following exemplary embodiment may be a description other than the character string. In addition, similarly, a "phrase" in the following exemplary embodiment may be a description other than the phrase.

Figure 1:
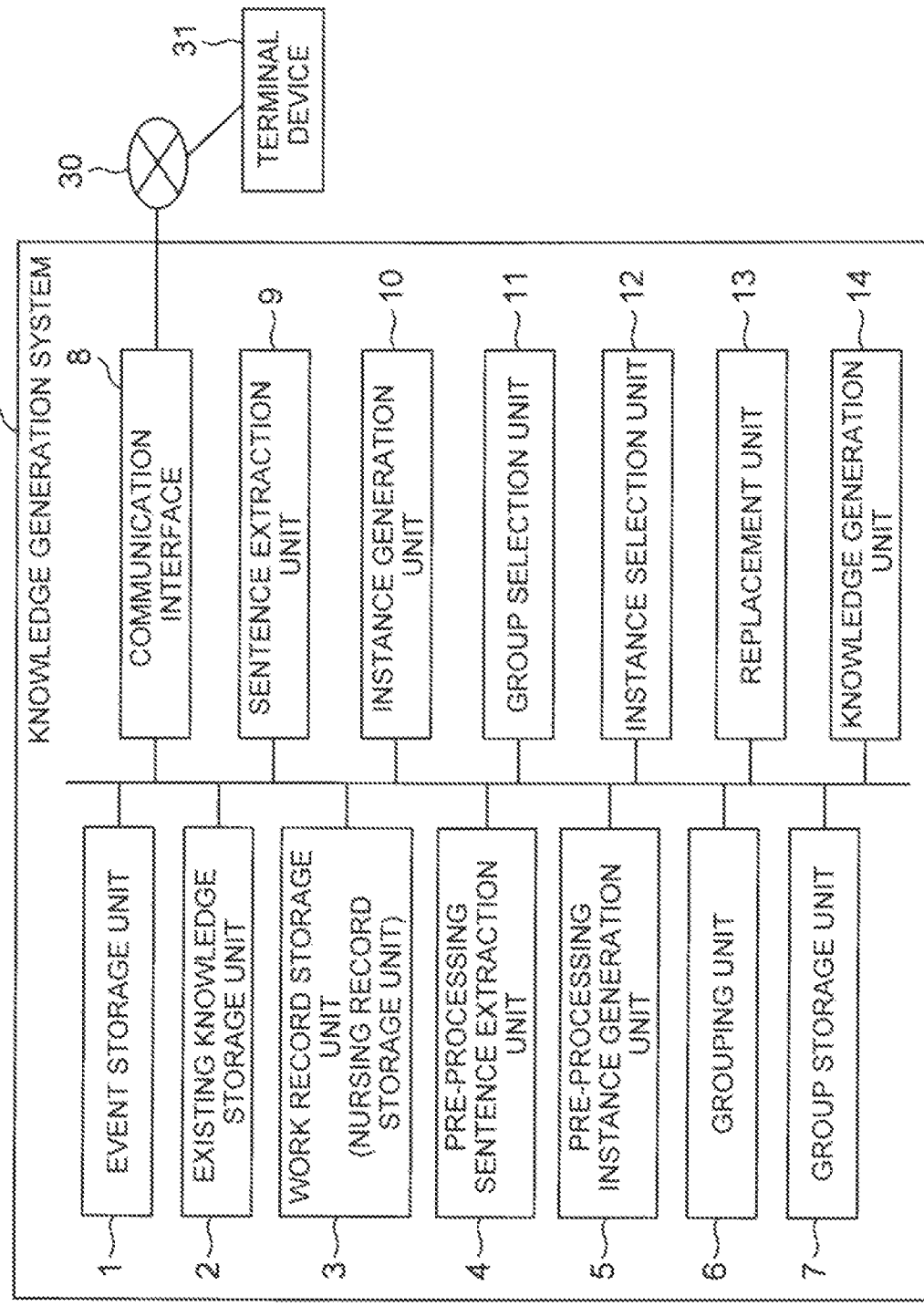
FIG. 1 It depicts a block diagram illustrating a configuration example of a knowledge generation system according to an exemplary embodiment of the present invention.

FIG. 1 is a block diagram illustrating a configuration example of a knowledge generation system 20 according to the exemplary embodiment of the present invention. The knowledge generation system 20 includes an event storage unit 1, an existing knowledge storage unit 2, a work record storage unit 3, a pre-processing sentence extraction unit 4, a pre-processing instance generation unit 5, a grouping unit 6, a group storage unit 7, a communication interface 8, a sentence extraction unit 9, an instance generation unit 10, a group selection unit 11, an instance selection unit 12, a replacement unit 13, and a knowledge generation unit 14.

Processing of the knowledge generation system 20 is roughly divided into pre-processing and knowledge generation processing. In the pre-processing, the knowledge generation system 20 generates instances based on past work records and groups the instances. The instance will be described later. In the knowledge generation processing, the knowledge generation system 20 newly creates knowledge when a new work record is created by a worker.

The present invention is applicable to work in which work record creation is included in a series of work. Hereinafter, a case where the present invention is applied to work of a nurse will be described as an example in order to facilitate understanding of the description. In this case, the nurse corresponds to the worker. In addition, a work record is referred to as a nursing record in the following description.

In accordance with this, the work record storage unit 3 will be referred to as the nursing record storage unit 3 for convenience, hereinafter.

In addition, the knowledge generation system 20 communicates with a terminal device 31 via a communication network 30. The terminal device 31 is used by the nurse. The terminal device 31 is a terminal device provided with a display device (not illustrated) and capable of inputting characters. Examples of the terminal device 31 include a personal computer, a smartphone, a tablet terminal, and the like. Examples of the communication network 30 include a local area network (LAN), the Internet, and the like, but the communication network 30 is not limited to these examples. Although the single terminal device 31 is illustrated in FIG. 1, a plurality of the terminal devices 31 communicating with the knowledge generation system 20 may exist.

The event storage unit 1 is a storage device that stores a predetermined event. There may be a plurality of predetermined events, and the event storage unit 1 may store the plurality of events. For example, the event storage unit 1 stores events such as "SAT decrease", "blood pressure decrease", and "pulse decrease". The event stored in the event storage unit 1 is represented by a character string. Note that "SAT decrease" means a decrease of blood oxygen concentration. In the following description, the description will be given by paying attention to "SAT decrease".

Note that the "event" may be referred to as a "scene".

Figure 2:
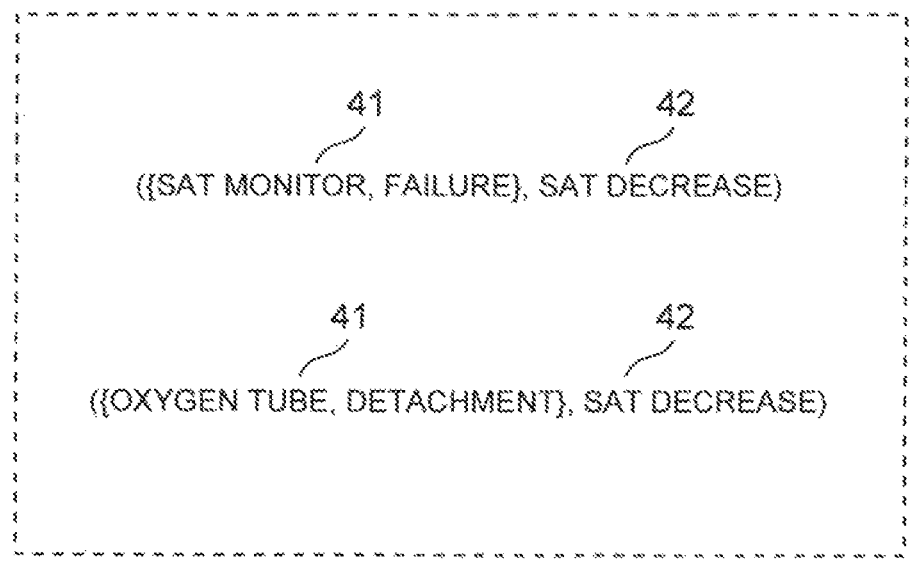
FIG. 2 It depicts an explanatory view illustrating an example of existing knowledge.

The existing knowledge storage unit 2 is a storage device that stores existing knowledge in advance. As described above, knowledge is information that represents a cause or a coping method for an event. FIG. 2 is an explanatory view illustrating an example of existing knowledge stored in the existing knowledge storage unit 2. In the example illustrated in FIG. 2, each knowledge is represented by a pair of a character string 42 representing an event and one or more words 41 representing a cause or coping method corresponding to the event. In the example illustrated in FIG. 2, the one or more words 41 indicating the cause or coping method corresponding to the event are illustrated by curly brackets. The first knowledge illustrated in FIG. 2 represents that the cause of the SAT decrease is a failure of a SAT monitor. In addition, the second knowledge illustrated in FIG. 2 represents that the cause of the SAT decrease is detachment of an oxygen tube. Although FIG. 2 illustrates the knowledge representing the cause of the event, existing knowledge representing the coping method for the event may be stored in the existing knowledge storage unit 2. In addition, the existing knowledge of the event other than the SAT decrease may be stored in the existing knowledge storage unit 2.

The nursing record storage unit 3 is a storage device that stores past nursing records that have been created so far. The nursing record storage unit 3 stores a nursing record represented by text data. However, the nursing record stored in the nursing record storage unit 3 may be created as text data from the beginning, or may be converted from voice data to text data. The nursing record includes a plurality of sentences.

The pre-processing sentence extraction unit 4 extracts a sentence related to a predetermined event, the sentence containing a different content from the existing knowledge corresponding to the event, from the nursing records created in the past (that is, the nursing records stored in the nursing record storage unit 3).

The predetermined event is an event stored in the event storage unit 1. Here, a description will be given assuming that the predetermined event is "SAT decrease". Note that, when there are a plurality of predetermined events, the knowledge generation system 20 may perform the same processing for each of the predetermined events.

The pre-processing sentence extraction unit 4 determines whether or not a sentence is related to the predetermined event as follows. The pre-processing sentence extraction unit 4 determines that a sentence including all of words included in the character string representing the event is the sentence related to the event. In addition, the pre-processing sentence extraction unit 4 determines that a sentence including only some of the words included in the character string representing the event or a sentence including none of the words is a sentence not related to the event. For example, the character string "SAT decrease" includes the words "SAT" and "decrease". Therefore, the pre-processing sentence extraction unit 4 determines that the sentence including all the words "SAT" and "decrease" is the sentence related to "SAT decrease". In addition, the pre-processing sentence extraction unit 4 determines that a sentence including only one of the words "SAT" and "decrease" or a sentence not including the both is the sentence not related to "SAT decrease".

In addition, the pre-processing sentence extraction unit 4 determines whether or not the sentence contains a different content from the existing knowledge corresponding to the event as follows. The pre-processing sentence extraction unit 4 determines that a sentence including only some words among one or more words 41 indicating a cause or a coping method included in the existing knowledge corresponding to the event or including none of the words is a sentence containing a different content from the existing knowledge. In addition, the pre-processing sentence extraction unit 4 determines that a sentence including all of the one or more words 41 indicating the cause or coping method included in the existing knowledge corresponding to the event is a sentence containing the same content as the existing knowledge. For example, the first knowledge illustrated in FIG. 2 will be described as an example. If a sentence included in the past nursing records includes only one of the two words "SAT monitor" and "failure" or does not include the both, the pre-processing sentence extraction unit 4 determines that the sentence is a sentence containing the different content from the knowledge. In addition, if a sentence includes both the two words "SAT monitor" and "failure", the pre-processing sentence extraction unit 4 determines that the sentence contains the same content as the knowledge.

For each sentence included in the past nursing records, the pre-processing sentence extraction unit 4 determines whether or not the sentence is related to the predetermined event, and determines whether or not the sentence contains the different content from the existing knowledge corresponding to the event, and extracts the sentence related to the predetermined event, the sentence containing the different content from the existing knowledge corresponding to the event.

FIG. 3 illustrates an example of the sentence extracted by the pre-processing sentence extraction unit 4. Both Sentence 1 and Sentence 2 illustrated in FIG. 3 include both the words "SAT" and "decrease". In addition, Sentence 1 and Sentence 2 do not include the words "SAT monitor" and "failure" in the first existing knowledge illustrated in FIG. 2, and do not include the words "oxygen tube" and "detachment" in the second existing knowledge illustrated in FIG. 2. Therefore, Sentence 1 and Sentence 2 are both the sentences related to the event "SAT decrease" and contain the different content from the two pieces of existing knowledge illustrated in FIG. 2.

The pre-processing instance generation unit 5 generates an event phrase removal character string obtained by removing a phrase representing the event from the sentence extracted by the pre-processing sentence extraction unit 4. The event phrase removal character string is a character string obtained by removing the phrase representing the event from the extracted sentence. The event phrase removal character string can be generated by removing the phrase representing the event from the extracted sentence. In the following description, the event phrase removal character string is referred to as an instance. It can be said that the instance is a character string that is likely to represent a cause or coping method corresponding to the event.

In addition, the phrase representing the event is a phrase including all of words included in a character string representing the event. For example, the character string "SAT decrease" includes the words "SAT" and "decrease". In this case, the pre-processing instance generation unit 5 removes a phrase including the two words "SAT" and "decrease" from the sentence extracted by the pre-processing sentence extraction unit 4 to generate an instance.

For example, in Sentence 1 illustrated in FIG. 3, a phrase "due to SAT decrease" includes all the two words "SAT" and "decrease". Therefore, the pre-processing instance generation unit 5 deletes the phrase "due to SAT decrease" from Sentence 1 to generate an instance "perform sputum suction".

In addition, for example, in Sentence 2 illustrated in FIG. 3, the phrase "SAT decreased to 90%" includes all the two words "SAT" and "decrease". Therefore, the pre-processing instance generation unit 5 deletes the phrase "SAT decreased to 90%", from Sentence 2 to generate an instance "sputum was suctioned because breathing was difficult due to accumulated sputum".

Figure 4:
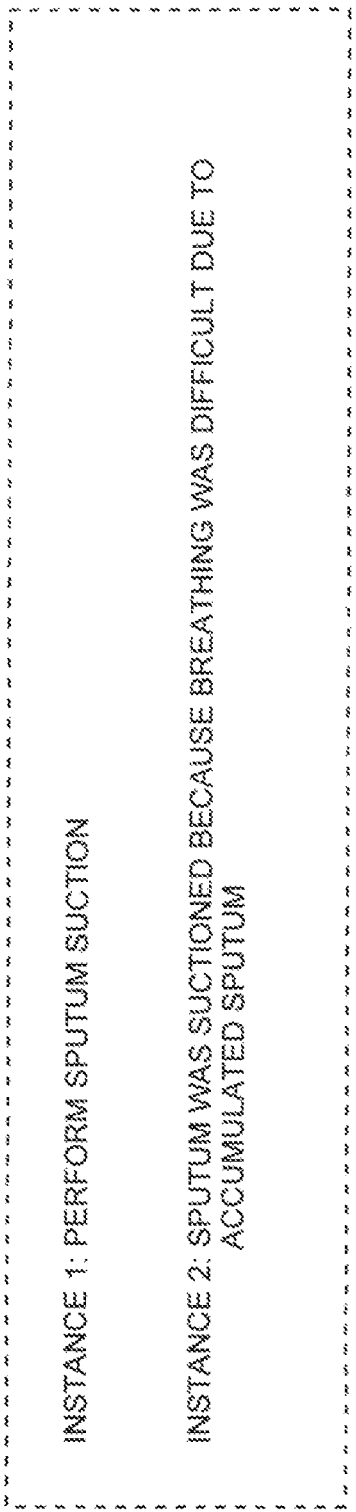
FIG. 4 It depicts an explanatory view illustrating an example of instances generated from Sentence 1 and Sentence 2 illustrated in FIG. 3.

FIG. 4 illustrates an example of the instance generated in this manner. Instances 1 and 2 illustrated in FIG. 4 are generated from Sentences 1 and 2 illustrated in FIG. 3. Although FIG. 4 illustrates two instances, the instances related to "SAT decrease" and are obtained based on the past nursing records are not limited to these two instances.

Note that the knowledge generation system 20 may hold a synonym dictionary of words. The pre-processing sentence extraction unit 4 may use a synonym of a word to determine whether or not a sentence is related to an event, and the pre-processing instance generation unit 5 may generate an instance using a synonym of a word.

The grouping unit 6 groups instances obtained by the pre-processing instance generation unit 5. The grouping unit 6 executes the grouping of instances for each event.

Figure 5:
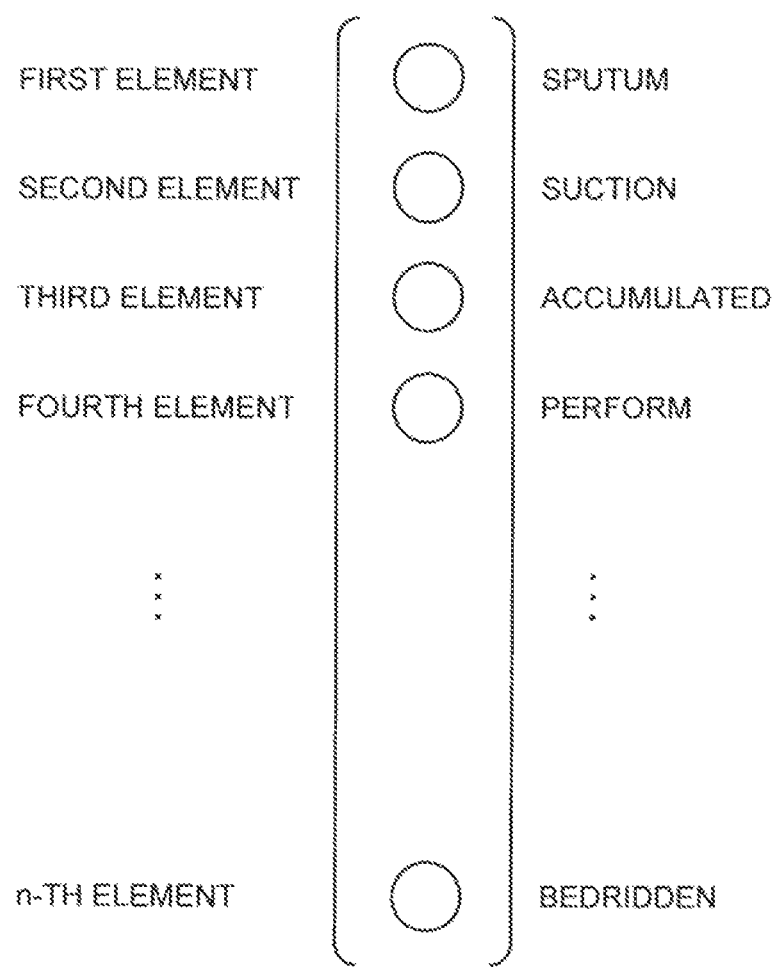
FIG. 5 It depicts an explanatory view illustrating an example of associating each element of an n-dimensional vector with a word.

First, the grouping unit 6 defines a vector representing an instance for each instance. Hereinafter, an operation in which the grouping unit 6 defines a vector representing an instance will be described. It is assumed that the vector representing the instance is an n-dimensional vector. Each element of the n-dimensional vector corresponds to a pre-determined word. FIG. 5 is an explanatory view illustrating an example of associating each element of the n-dimensional vector with a word. In the example illustrated in FIG. 5, the first element of the n-dimensional vector is defined to correspond to "sputum". Similarly, the second element is defined to correspond to "suction" the third element is defined to correspond "accumulated", the fourth element is defined to correspond to "perform", and the n-th element is defined to correspond to "bedridden".

The grouping unit 6 defines a value of the first element to "1" if the word corresponding to the first element ("sputum" in the above example) is included in an instance of interest, and defines the value of the first element to "0" if the word corresponding to the first element is not included in the instance of interest. The grouping unit 6 also performs this process for each of the second to n-th elements. As a result, the vector representing the instance is obtained. For example, in the above example, a vector $(1, 1, 0, 1, 0, \ldots, 0)^T$ is obtained for the instance "perform sputum suction". Note that T means transpose.

The grouping unit 6 defines the vectors for the respective instances obtained for the event "SAT decrease" as described above. All the vectors representing the individual instances are n-dimensional vectors.

The grouping unit 6 groups the individual instances based on the individual vectors representing the individual instances obtained for "SAT decrease". More specifically, the grouping unit 6 groups the instances obtained for "SAT decrease" such that instances are included in the same group if a distance between vectors representing the instances is close, and instances are included in different groups if a distance between vectors representing the instances is far. It can be said that the vectors are grouped in such a grouping method, and a representative example of such a grouping method is the K-means method. In addition, when vectors are grouped by the K-means method, a vector representing a center of a group can also be defined. As will be described later, a grouping method that can also define a vector representing the center of each group may be adopted in the case of using the vector representing the center of the group, and a representative example thereof is the K-means method. In the following description, a case where the grouping unit 6 groups individual vectors representing individual instances obtained for "SAT decrease" by the K-means method to group the individual instances will be described as an example. However, the grouping unit 6 may group instances by a method other than the K-means method as long as the instances are grouped based on individual vectors representing individual instances by the method.

In addition, when there occurs an instance that is not included in any group, the grouping unit 6 may define a group that includes only the instance.

Figure 6:
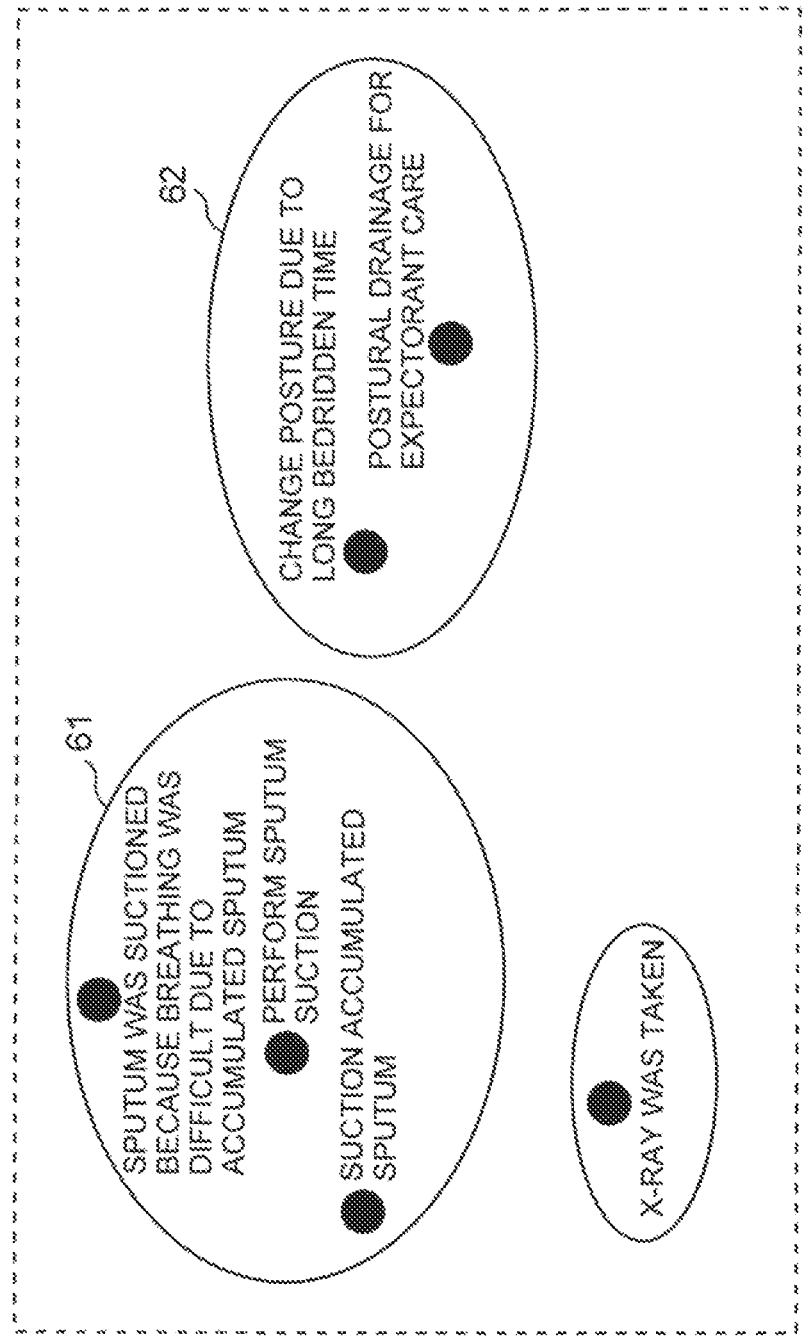
FIG. 6 It depicts a schematic view illustrating an example of a group defined by a grouping unit.

FIG. 6 illustrates an example of a group (group of an instance) defined by the grouping unit 6.

The grouping unit 6 stores each of groups of instances, obtained as a result of grouping, in the group storage unit 7.

The group storage unit 7 is a storage device that stores each of the groups of instances obtained as the result of grouping.

In other words, the group storage unit 7 stores the groups of instances obtained by grouping the instances which are likely to represent a cause or a coping method corresponding to an event and are obtained from the past nursing records.

In the present exemplary embodiment, the grouping unit 6 groups the instances by grouping vectors by, for example, the K-means method, and also stores a vector representing the center of each group in the group storage unit 7 when the vector representing the center of the group is used in the knowledge generation processing.

A group is obtained by grouping character string candidates for knowledge generation.

A process until the grouping unit 6 stores a grouping result in the group storage unit 7 corresponds to the pre-processing.

The communication interface 8 is a communication interface when the knowledge generation system 20 communicates with the terminal device 31 via the communication network 30.

The creation of the nursing record by the nurse will be described before describing the sentence extraction unit 9. For example, the nurse performs work of creating the nursing record during work every day. At this time, the nurse creates the nursing record using the terminal device 31. As described above, the terminal device 31 is the terminal device including the display device (not illustrated) and capable of inputting characters. A mode of the character input may be character input using a keyboard (not illustrated), or may be an input mode in which a voice input by a microphone (not illustrated) is converted into characters. The nurse inputs characters to create a new nursing record. At this time, the creation of the nursing record is completed by performing an operation of confirming the nursing record. The confirmation operation may be an operation performed by the nurse himself/herself, or may be an approval operation performed by the nurse's boss. Hereinafter, a case where the nurse himself/herself performs the confirmation operation will be described as an example for the sake of simplicity.

Before the confirmation operation, the terminal device 31 displays a nursing record (unconfirmed nursing record) represented by an input character string on the display device, and transmits the unconfirmed nursing record to the knowledge generation system 20 appropriately via the communication network 30.

The sentence extraction unit 9 receives the unconfirmed nursing record via the communication interface 8. Then, the sentence extraction unit 9 extracts a sentence related to a predetermined event (event stored in the event storage unit 1), the sentence including a content different from existing knowledge corresponding to the event, from the undetermined nursing record. As described above, when there are a plurality of predetermined events, the knowledge generation system 20 may perform the same processing for each of the predetermined events.

A process of determining whether or not a sentence is related to the predetermined event performed by the sentence extraction unit 9 is the same as the determination process performed by the pre-processing sentence extraction unit 4. That is, the sentence extraction unit 9 determines that a sentence including all of words included in the character string representing the event is the sentence related to the event. In addition, the sentence extraction unit 9 determines that a sentence including only some of the words included in the character string representing the event or including none of the words is a sentence not related to the event.

A process of determining whether or not a sentence contains a different content from the existing knowledge corresponding to the event performed by the sentence extraction unit 9 is also the same as the determination process performed by the pre-processing sentence extraction unit 4. That is, the sentence extraction unit 9 determines that a sentence including only some words among one or more words 41 (see FIG. 2) indicating a cause or a coping method included in the existing knowledge corresponding to the event or including none of the words is a sentence containing a different content from the existing knowledge. In addition, the sentence extraction unit 9 determines that a sentence including all of the one or more words 41 indicating the cause or coping method included in the existing knowledge corresponding to the event is a sentence containing the same content as the existing knowledge.

For each sentence included in the unconfirmed nursing record, the sentence extraction unit 9 determines whether or not the sentence is related to the predetermined event, and determines whether or not the sentence contains the different content from the existing knowledge corresponding to the event, and extracts the sentence related to the predetermined event, the sentence containing the different content from the existing knowledge corresponding to the event.

Figure 7:
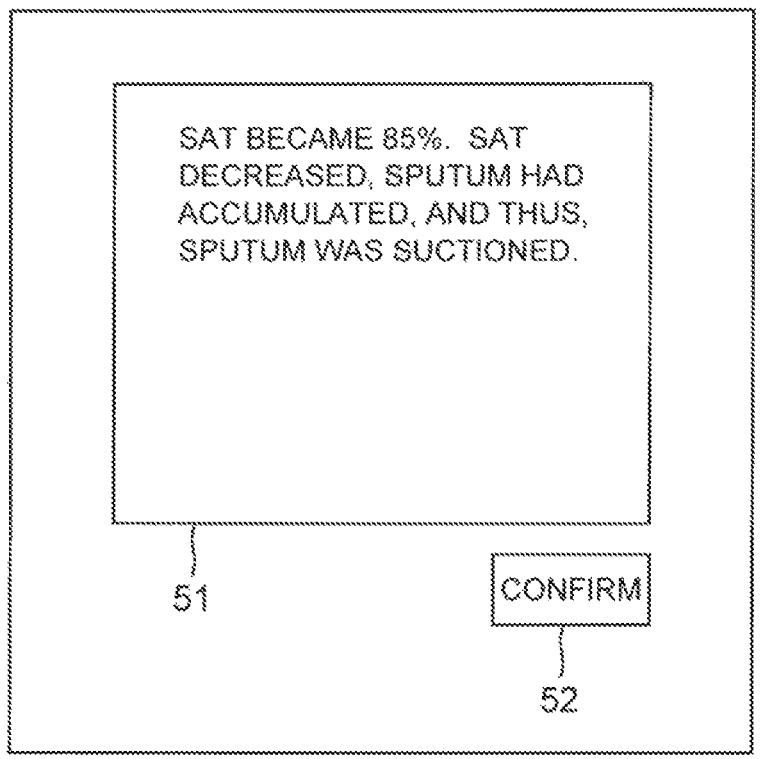
FIG. 7 It depicts a schematic view illustrating an example of an unconfirmed nursing record displayed on a display device of a terminal device.

FIG. 7 is a schematic view illustrating an example of the unconfirmed nursing record displayed on the display device of the terminal device 31. The terminal device 31 displays a nursing record input by the nurse in a record display field 51 in a screen. A confirmation button 52 is a graphical user interface (GUI) configured for the nurse to perform a confirmation operation. Before the confirmation button 52 is clicked, the terminal device 31 transmits the nursing record (unconfirmed nursing record) displayed in the record display field 51 to the knowledge generation system 20.

It is assumed that the sentence extraction unit 9 receives the unconfirmed nursing record illustrated in FIG. 7 from the terminal device 31. In the nursing record illustrated in FIG. 7, the sentence "SAT decreased, sputum had accumulated, and thus, sputum was suctioned" (hereinafter referred to as Sentence A) includes both the words "SAT" and "decrease". Therefore, the sentence extraction unit 9 determines that the Sentence A is the sentence related to "SAT decrease".

In addition, Sentence A does not include the words "SAT monitor" and "failure" in the first existing knowledge illustrated in FIG. 2, and does not include the words "oxygen tube" and "detachment" in the second existing knowledge illustrated in FIG. 2. Therefore, the sentence extraction unit 9 determines that Sentence A is the sentence containing a different content from the two pieces of existing knowledge illustrated in FIG. 2.

Therefore, in this example, the sentence extraction unit 9 extracts Sentence A as the sentence that is related to "SAT decrease" and contains the different content from the existing knowledge (see FIG. 2) corresponding to "SAT decrease".

The instance generation unit 10 generates an event phrase removal character string (instance) obtained by removing a phrase representing an event from the sentence extracted by the sentence extraction unit 9. As described above, the event phrase removal character string is a character string obtained by removing the phrase representing the event from the extracted sentence. In addition, the event phrase removal character string is referred to as an instance.

A process of generating the instance performed by the instance generation unit 10 is the same as the process of generating the instance performed by the pre-processing instance generation unit 5. That is, the instance generation unit 10 may generate the instance by removing a phrase that includes all of words included in a character string representing the event from the sentence extracted by the sentence extraction unit 9. For example, a phrase "SAT decreased" included in Sentence A described above includes all the two words "SAT" and "decrease". The phrase "SAT decreased" is a phrase that represents the event "SAT decrease". Accordingly, in this example, the instance generation unit 10 generates an instance "sputum had accumulated, and thus, sputum was suctioned" by removing the phrase "SAT decreased" from Sentence A. Hereinafter, the instance generated by the instance generation unit 10 is indicated by reference sign X.

The group selection unit 11 selects one group including a plurality of instances from groups stored in the group storage unit 7 based on a similarity between each of groups including a plurality of instances among the groups stored in the group storage unit 7 by the pre-processing and the instance X. Therefore, a group including only one instance is not selected. For example, it is assumed that three groups schematically illustrated in FIG. 6 are derived for the event "SAT decrease". Among the three groups illustrated in FIG. 6, one group includes only one instance (see FIG. 6). The group including only one instance in this manner is excluded from selection targets of the group selection unit 11.

In the present exemplary embodiment, the group selection unit 11 defines a vector representing the instance X. An operation of defining the vector representing the instance X performed by the group selection unit 11 is the same as the operation of defining the vector representing the instance performed by the grouping unit 6, and thus, the description thereof will be omitted. Then, the group selection unit 11 calculates a distance between each of vectors representing centers of groups including a plurality of instances, and the vector representing the instance X as the similarity between each group and the instance X. In this case, a smaller distance means a higher similarity, and a larger distance means a lower similarity. The group selection unit 11 selects a group having the highest similarity with the instance X. In other words, the group selection unit 11 selects a group having the minimum distance between the vector representing the instance X and the vector representing the center of the group. Hereinafter, a distance between two vectors is expressed as the distance of the two vectors.

Among the three groups schematically illustrated in FIG. 6, groups 61 and 62 are groups including a plurality of instances. Therefore, the group selection unit 11 calculates each of a distance between a vector representing a center of the group 61 and the vector representing the instance X, and a distance between a vector representing a center of the group 62 and the vector representing the instance X. Then, the group selection unit 11 selects a group corresponding to the minimum distance.

In this example, it is assumed that the instance X is "sputum had accumulated, and thus, sputum was suctioned", and the group selection unit 11 selects the group 61.

The instance selection unit 12 selects one instance from the group selected by the group selection unit 11.

For example, the instance selection unit 12 may select an instance having a highest similarity with the instance X from the selected group. In this case, the instance selection unit 12 calculates a distance between each vector representing each instance included in the group and the vector representing the instance X. As described above, a smaller distance means a higher similarity, and a larger distance means a lower similarity. The instance selection unit 12 may select an instance corresponding to the vector having the minimum distance from the vector representing the instance X. Note that a method by which the instance selection unit 12 selects the instance is not limited to the above method.

For example, the instance selection unit 12 may select a character string from the selected group based on a length of each character string included in the group. Specifically, the instance selection unit 12 may select the instance having the minimum length from the group. The length of the instance may be defined as the number of characters included in the instance, or may be defined as the number of words included in the instance.

In addition, for example, the instance selection unit 12 may select an instance from the selected group based on a distance between the vector representing the center of the group and each of vectors representing instances included in the group. Specifically, the instance selection unit 12 may calculate each distance between the vector representing the center of the selected group and each of the vectors representing the instances included in the group and select the instance having the minimum distance.

In addition, there are a plurality of nurses in general, and each of the nurses creates a nursing record using the terminal device 31 possessed by himself/herself. In addition, each of the nurses creates the nursing record, for example, every day. Therefore, the same group may be selected a plurality of times by the group selection unit 11, for example, for the event "SAT decrease".

When the same group is selected a plurality of times by the group selection unit 11, two modes are conceivable as a mode in which the instance selection unit 12 selects an instance from the group.

A first instance selection mode is a selection mode in which when the same group is selected a plurality of times, the instance selection unit 12 selects an instance from the group while allowing an instance selected once to be selected again.

A second instance selection mode is a selection mode in which when the same group is selected a plurality of times, the instance selection unit 12 selects an instance from the group without allowing an instance selected once to be selected again. In other words, the second instance selection mode is the selection mode in which the instance selection unit 12 selects an instance different from an instance selected once when the same group is selected a plurality of times. In the second selection mode, the instance selection unit 12 excludes the instance selected once from selection targets. Then, the instance selection unit 12 selects an instance from among the remaining instances (that is, unselected instances) that have not been excluded from among the instances included in the group. As described above, a method for selecting an instance may be the method of selecting the instance having the highest similarity with the instance X, may be the method of selecting the instance having the minimum length, or may be a method of calculating each distance between a vector representing a center of a group and each of vectors representing instances included in the group and selecting an instance having the minimum distance.

In the present exemplary embodiment, the first instance selection mode can be adopted, and the second instance selection mode can also be adopted.

Hereinafter, the instance selected by the instance selection unit 12 is indicated by reference sign Y. Here, it is assumed that the instance X is "sputum had accumulated, and thus, sputum was suctioned", and the instance Y selected from the group 61 by the instance selection unit 12 is "sputum was suctioned because breathing was difficult due to accumulated sputum".

The replacement unit 13 replaces the instance X included in an unconfirmed nursing record received from the terminal device 31 with the instance Y. At this time, the replacement unit 13 emphasizes a replaced character string (that is, instance Y), for example, as a colored character string or an underlined character string in the nursing record after replacement. Note that, when the instance Y and the instance X include a common character string, only a character string corresponding to a difference between the instance Y and the instance X may be emphasized. Hereinafter, a case where the replacement unit 13 emphasizes the entire instance Y as an underlined character string will be described as an example for the sake of simplicity.

The replacement unit 13 transmits the nursing record in which the instance X has been replaced with the instance Y as described above to the terminal device 31 via the communication interface 8.

Figure 8:
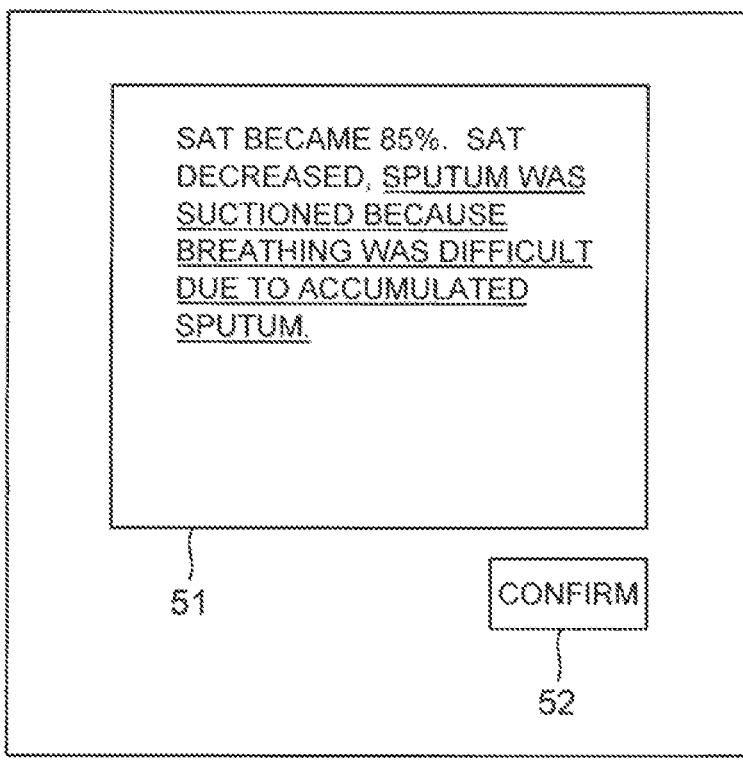
FIG. 8 It depicts is a schematic view illustrating an example of a nursing record after replacement displayed on the display device of the terminal device.

The terminal device 31 that has received the nursing record after replacement displays this nursing record after replacement on the display device. FIG. 8 is a schematic view illustrating an example of the nursing record after replacement displayed on the display device of the terminal device 31. In the example illustrated in FIG. 8, a character string "sputum had accumulated, and thus, sputum was suctioned" in FIG. 7 (the instance X in the above example) is replaced with a character string "sputum was suctioned because breathing was difficult due to accumulated sputum" (the instance Y in the above example), and the replaced character string is underlined.

The nurse does not need to recognize the operation of the knowledge generation system 20 that has received the unconfirmed nursing record from the terminal device 31, and may continue to create the nursing record while confirming the nursing record after replacement on the display device. If the replaced character string (character string corresponding to the instance Y) has an expression or wording different from the intention of the nurse in the nursing record after replacement, this wording may be corrected. In addition, the nurse may make a correction to return the entire replaced character string to the original character string (character string corresponding to the instance X). Alternatively, the nurse may continue to create the nursing record without correcting the replaced character string if the replaced character string has no expression or wording that is different from the intention of the nurse.

When it is determined that the creation of the nursing record has been completed and the content of the new nursing record has been confirmed, the nurse clicks the confirmation button 52. When the confirmation button 52 is clicked, the terminal device 31 transmits, to the knowledge generation system 20, information indicating that the nursing record has been confirmed, the confirmed nursing record, and information indicating whether or not the character string replaced by the replacement unit 13 has been corrected by the nurse.

Figure 9:
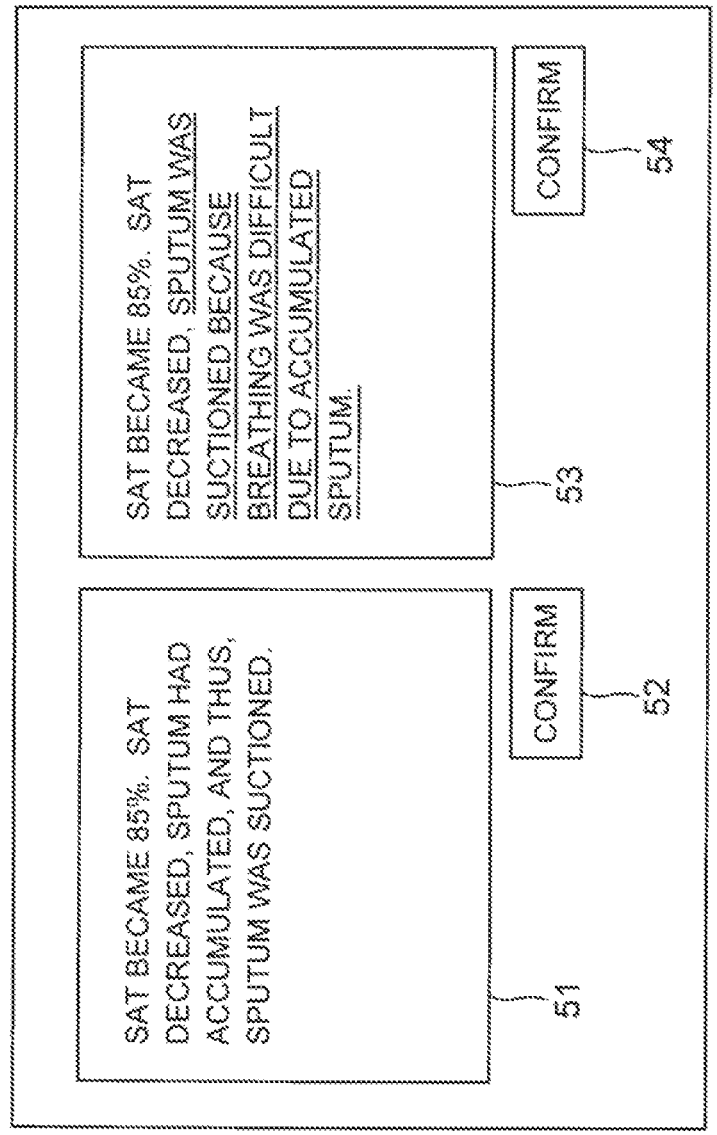
FIG. 9 It depicts a schematic view illustrating another example of a display screen of the nursing record after replacement.

Note that a display screen of the nursing record after replacement is not limited to the example illustrated in FIG. 8. FIG. 9 is a schematic view illustrating another example of the display screen of the nursing record after replacement. In the example illustrated in FIG. 9, the terminal device 31 displays a nursing record before replacement in the record display field 51, and displays a second record display field 53 to display the nursing record after replacement in the second record display field 53. In addition, the terminal device 31 also displays a confirmation button 54 corresponding to the second record display field 53 in addition to the confirmation button 52 corresponding to the record display field 51. The terminal device 31 edits the nursing record in the record display field 51 or the nursing record in the second record display field 53 in response to the nurse's operation.

In the example illustrated in FIG. 9, it is assumed that the nurse has edited the nursing record in the record display field 51 and clicked the confirmation button 52. This is synonymous with making a correction to return the replaced character string to the original character string, continuing to create a nursing record, and confirming the nursing record. Therefore, in this case, the terminal device 31 transmits, to knowledge generation system 20, information indicating that the nursing record has been confirmed, the confirmed nursing record, and information indicating that the character string replaced by the replacement unit 13 has been corrected by the nurse.

In addition, the nurse may edit the nursing record in the second record display field 53 in the example illustrated in FIG. 9. Then, the nurse may correct the replaced character string or does not necessarily correct the replaced character string. This point is similar to the case of continuing to create a nursing record on the screen illustrated in FIG. 8. Then, when the confirmation button 54 is clicked, the terminal device 31 transmits, to knowledge generation system 20, information indicating that the nursing record has been confirmed, the confirmed nursing record, and information indicating whether or not the character string replaced by the replacement unit 13 has been corrected by the nurse. Whether the information indicating that the replaced character string has been corrected by the nurse or the information indicating that the replaced character string has not been corrected by the nurse depends on whether the nurse has corrected the replaced character string.

The knowledge generation unit 14 receives the above-described pieces of information transmitted by the terminal device 31 (the information indicating that the nursing record has been confirmed, the confirmed nursing record, and the information indicating whether or not the character string replaced by the replacement unit 13 has been corrected by the nurse) via the communication interface 8.

The knowledge generation unit 14 stores the confirmed nursing record in the nursing record storage unit 3.

In addition, when a predetermined condition regarding a confirmation status of the nursing record in which the instance X has been replaced with the instance Y is confirmed is satisfied, the knowledge generation unit 14 selects an instance from a group including the instance Y (the group 61 illustrated in FIG. 6 in the above example), and generates new knowledge based on the instance.

As described above, there are a plurality of nurses in general, and each of the nurses creates a nursing record using the terminal device 31 possessed by himself/herself. In addition, each of the nurses creates the nursing record, for example, every day. Therefore, the same group may be selected a plurality of times by the group selection unit 11, for example, for the event "SAT decrease".

Further, when the instance selection unit 12 selects an instance from the group while allowing the instance selected once to be selected again (the first instance selection mode), the same instance can be selected a plurality of times. In addition, when the instance selection unit 12 selects an instance from the group without allowing the instance selected once to be selected again (the second instance selection mode), the same instance is not selected a plurality of times.

Based on these points, a description will be given regarding examples of the predetermined condition regarding the situation in which the nursing record in which instance X has been replaced with instance Y is confirmed, and an example of a method by which the knowledge generation unit 14 selects an instance from a group.

First, an example of a case in which the first instance selection mode is adopted will be described.

Example 1

The predetermined condition may be a condition that "the same instance has been selected a plurality of times from the same group by the instance selection unit 12, and a nursing record, in which the instance X has been replaced with such an instance, has been confirmed a predetermined number of times by the nurse without any correction to the instance".

In this case, when the above-described predetermined condition is satisfied, the knowledge generation unit 14 selects the above-described instance, which has been selected the plurality of times from the above-described group, and generates new knowledge based on the instance.

For the sake of simplicity, the "predetermined number of times" will be described as "three times". This point is similarly applied even in examples to be described later.

The present example will be specifically described with reference to FIG. 6. It is assumed that the instance "sputum was suctioned because breathing was difficult due to accumulated sputum" has been selected by the instance selection unit 12 a plurality of times from the group 61 illustrated in FIG. 6. Here, this instance is referred to as an instance α. Then, it is assumed that a nursing record in which the instance X has been replaced with the instance α has been confirmed by the nurse three times without any correction to the instance α. In this case, the above-described predetermined condition is satisfied. In this case, the knowledge generation unit 14 selects the instance α from the group 61 illustrated in FIG. 6 and generates new knowledge based on the instance α.

Example 2

The predetermined condition may be a condition that "an instance has been selected a plurality of times from the same group by the instance selection unit 12, and a nursing record, in which the instance X has been replaced with the selected instance, has been confirmed a predetermined number of times by the nurse without any correction to the selected instance".

In this case, when the above predetermined condition is satisfied, the knowledge generation unit 14 selects an instance that has been most frequently selected by the instance selection unit 12 from the above group, and generates new knowledge based on the instance.

The present example will be specifically described with reference to FIG. 6. It is assumed that the instance (instance α) "sputum was suctioned because breathing was difficult due to accumulated sputum" has been selected by the instance selection unit 12 once from the group 61 illustrated in FIG. 6. Then, it is assumed that a nursing record in which the instance X has been replaced with the instance α has been confirmed by the nurse once without any correction to the instance α. In addition, it is assumed that an instance "perform sputum suction" has been selected twice by the instance selection unit 12 from the group 61. This instance is referred to as an instance β. Then, it is assumed that a nursing record in which the instance X has been replaced with the instance β has been confirmed by the nurse twice without any correction to the instance β.

Then, the nursing record in which the instance X has been replaced with the selected instance is confirmed by the nurse three times without any correction to the selected instance. Therefore, the predetermined condition is satisfied. In the above example, the instance α is selected once, and the instance β is selected twice. Therefore, the knowledge generation unit 14 selects the instance β that has been most frequently selected from the group 61, and generates new knowledge based on the instance β.

In "Example 3", "Example 4", and "Example 5" illustrated below, the first instance selection mode may be adopted, or the second instance selection mode may be adopted.

Example 3

The predetermined condition may be a condition that "an instance has been selected a plurality of times from the same group by the instance selection unit 12, and a nursing record, in which the instance X has been replaced with the selected instance, has been confirmed a predetermined number of times by the nurse without any correction to the selected instance". That is, the predetermined condition in Example 3 is the same as the predetermined condition in Example 2.

In the present example, when the above predetermined condition is satisfied, the knowledge generation unit 14 selects an instance from a group based on a length of each instance included in the group. Specifically, the knowledge generation unit 14 selects an instance having the minimum length from the group. Then, the knowledge generation unit 14 generates new knowledge based on the selected instance.

As described above, the length of the instance may be defined as the number of characters included in the instance, or may be defined as the number of words included in the instance.

The present example will be specifically described with reference to FIG. 6. It is assumed that the instance (instance α) "sputum was suctioned because breathing was difficult due to accumulated sputum" has been selected by the instance selection unit 12 once from the group 61 illustrated in FIG. 6. Then, it is assumed that a nursing record in which the instance X has been replaced with the instance α has been confirmed by the nurse once without any correction to the instance α. In addition, it is assumed that the instance (instance β) "perform sputum suction" has been selected once by the instance selection unit 12 from the group 61. Then, it is assumed that a nursing record in which the instance X has been replaced with the instance β has been confirmed by the nurse once without any correction to the instance β. In addition, it is assumed that the instance "suction accumulated sputum" has been selected once by the instance selection unit 12 from the group 61. This instance is set as an instance γ. Then, it is assumed that a nursing record in which the instance X has been replaced with the instance γ has been confirmed by the nurse once without any correction to the instance γ.

Then, the nursing record in which the instance X has been replaced with the selected instance is confirmed by the nurse three times without any correction to the selected instance. Therefore, the predetermined condition is satisfied. Although the cases where each of the instances α, β, and γ is selected once are illustrated in the above examples, one instance may be selected a plurality of times.

When the predetermined condition is satisfied as described above, the knowledge generation unit 14 selects the instance having the minimum instance length from among the instances included in the group 61. In the present example, the knowledge generation unit 14 selects the instance β ("perform sputum suction") having the minimum length from the group 61, and generates new knowledge based on the instance β.

In Example 3, the knowledge generation unit 14 selects a concise instance, and thus, can generate concise knowledge.

Example 4

A predetermined condition in Example 4 is the same as the predetermined condition in Example 2 and Example 3, and thus, the description thereof will be omitted.

In Example 4, it is assumed that the grouping unit 6 groups individual vectors representing individual instances obtained for "SAT decrease" by the K-means method and also defines a vector representing a center of a group in the pre-processing. However, the K-means method is an example, and is a method for grouping instances based on individual vectors representing individual instances. A method other than the K-means method may be used as long as a grouping method can also define a vector representing a center of each group. These points are similarly applied even in Example 5 to be described later.

In Example 4, when the predetermined condition is satisfied, the knowledge generation unit 14 selects an instance from a group (here, the group 61 illustrated in FIG. 6) that includes the selected instance as follows. The knowledge generation unit 14 selects the instance from the group 61 based on a distance between a vector representing a center of the group 61 and each of vectors representing instances included in the group 61. More specifically, the knowledge generation unit 14 calculates each distance between the vector representing the center of the group 61 and each of the vectors representing the instances included in the group 61, and selects the instance having the minimum distance. Among the respective instances included in the group 61 illustrated in FIG. 6, the distance between the vector representing the center of the group 61 and the vector representing the instance β ("perform sputum suction") is the minimum. Therefore, the knowledge generation unit 14 selects the instance β and generates new knowledge based on the instance β.

Note that, if a vector representing a certain instance included in a group and a vector representing a center of the group coincide, a distance between the two vectors becomes zero, and this instance is selected. However, the instance represented by the vector corresponding to the center of the group does not always exist. Even in such a case, the knowledge generation unit 14 can select the instance closest to the center (center of gravity) of the group according to the method illustrated in Example 4.

In Example 4, the knowledge generation unit 14 selects a representative instance of the group, and thus, can generate knowledge that clearly represents a characteristic of the group.

Example 5

A predetermined condition in Example 4 is the same as the predetermined condition in Example 2, Example 3, and Example 5, and thus, the description thereof will be omitted.

In Example 5, when the predetermined condition is satisfied, the knowledge generation unit 14 selects an instance from a group (here, the group 61 illustrated in FIG. 6) that includes the selected instance as follows. The knowledge generation unit 14 selects the instance from the group 61 based on a distance between a vector representing a center of the group 61 and each of vectors representing instances included in the group 61 and a length of each of the instances included in the group 61. More specifically, the knowledge generation unit 14 calculates a sum of a distance between the vector representing the center of the group 61 and a vector representing an instance and a length of the instance, for each of the instances included in the group 61. At this time, the knowledge generation unit 14 may normalize the distance and the length obtained for each of the instances such that the maximum value is one. The knowledge generation unit 14 selects an instance from the group 61 that minimizes the sum calculated as described above, and generates new knowledge based on the instance.

Figures 10, 11:
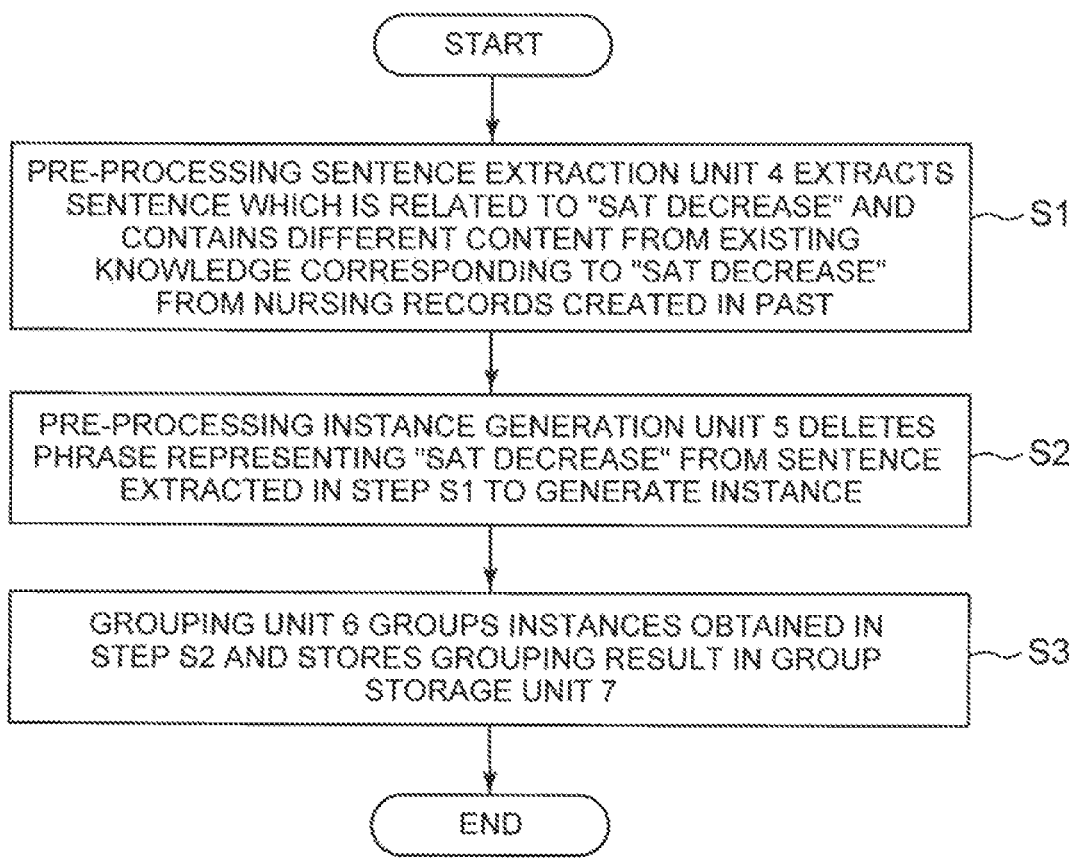
FIG. 10 It depicts a schematic view illustrating examples of distance and length obtained for each instance, and a sum of the both.
FIG. 11 It depicts a flowchart illustrating an example of a processing progress of pre-processing.

FIG. 10 is a schematic view illustrating examples of a distance, a length, and a sum of the both obtained for each instance. In the example illustrated in FIG. 10, each of the distance and the length is normalized such that the maximum value is one. For each instance, the sum of distance and length is calculated as illustrated in FIG. 10. In this case, the knowledge generation unit 14 selects the instance β having the smallest sum of distance and length, and generates new knowledge based on the instance β.

According to Example 5, both the effect of Example 3 and the effect of Example 4 can be obtained.

Next, an operation of generating new knowledge based on an instance selected by the knowledge generation unit 14 will be described. The knowledge generation unit 14 extracts individual words contained in the selected instance. In addition, the knowledge generation unit 14 uses a combination of an event of interest at the time of generating the instance and each of the extracted words as new knowledge. For example, it is assumed that the knowledge generation unit 14 selects the above-described instance β ("perform sputum suction."). In this case, the knowledge generation unit 14 extracts words "sputum", "suction", and "perform" from the instance β. In addition, an event of interest at the time of generating the instance β ("perform sputum suction") is "SAT decrease". Therefore, the knowledge generation unit 14 uses the combination of the respective extracted words and "SAT decrease" as new knowledge. Specifically, the knowledge generation unit 14 generates "({sputum, suction, perform}, SAT decrease)" as the new knowledge.

Note that the new knowledge becomes existing knowledge at the time of being generated. The knowledge generation unit 14 stores the generated new knowledge in the existing knowledge storage unit 2.

The pre-processing sentence extraction unit 4, the pre-processing instance generation unit 5, the grouping unit 6, the sentence extraction unit 9, the instance generation unit 10, the group selection unit 11, the instance selection unit 12, the replacement unit 13, and the knowledge generation unit 14 are realized, for example, by a central processing unit (CPU) which is a computer that operates according to a knowledge generation program. For example, the CPU may read the knowledge generation program from a program recording medium, such as a program storage device of the computer, and operate as the pre-processing sentence extraction unit 4, the pre-processing instance generation unit 5, the grouping unit 6, the sentence extraction unit 9, the instance generation unit 10, the group selection unit 11, the instance selection unit 12, the replacement unit 13, and the knowledge generation unit 14 according to the knowledge generation program.

The event storage unit 1, the existing knowledge storage unit 2, the work record storage unit 3, and the group storage unit 7 are realized by, for example, the storage device provided in the computer.

In addition, the terminal device 31 accesses the knowledge generation system 20 via the communication network 30, retrieves knowledge stored in the existing knowledge storage unit 2 using an event specified by the nurse as a key, and displays the knowledge obtained as the search result.

Next, an example of a processing progress of the present exemplary embodiment will be described. In the following description, a case where a predetermined event is "SAT decrease" will be described as an example. As described above, when there are a plurality of predetermined events, the knowledge generation system 20 may perform the same processing for each of the predetermined events.

FIG. 11 is a flowchart illustrating an example of a processing progress of pre-processing. Note that details of the items that have been already described will be omitted.

The knowledge generation system 20 executes the pre-processing, for example, every day at predetermined time in the morning (for example, 7:00). However, the execution timing of the pre-processing is not limited to this example, and may be, for example, any timing as long as the timing is earlier than a timing at which each nurse creates a nursing record for one day.

In the pre-processing, first, the pre-processing sentence extraction unit 4 extracts a sentence related to "SAT decrease" from nursing records created in the past, the sentence including a different content from existing knowledge corresponding to "SAT decrease" (for example, the existing knowledge illustrated in FIG. 2) (Step S1).

Next, the pre-processing instance generation unit 5 generates an instance by deleting a phrase representing "SAT decrease" from the sentence extracted in Step S1 (Step S2).

The number of sentences to be extracted in Step S1 is not limited to one, and a plurality of sentences can be extracted in Step S1. Therefore, a plurality of instances can be generated in Step S2.

Next, the grouping unit 6 groups the instances obtained in Step S2, and stores a grouping result (each group of instances) in the group storage unit 7 (Step S3).

Figure 12:
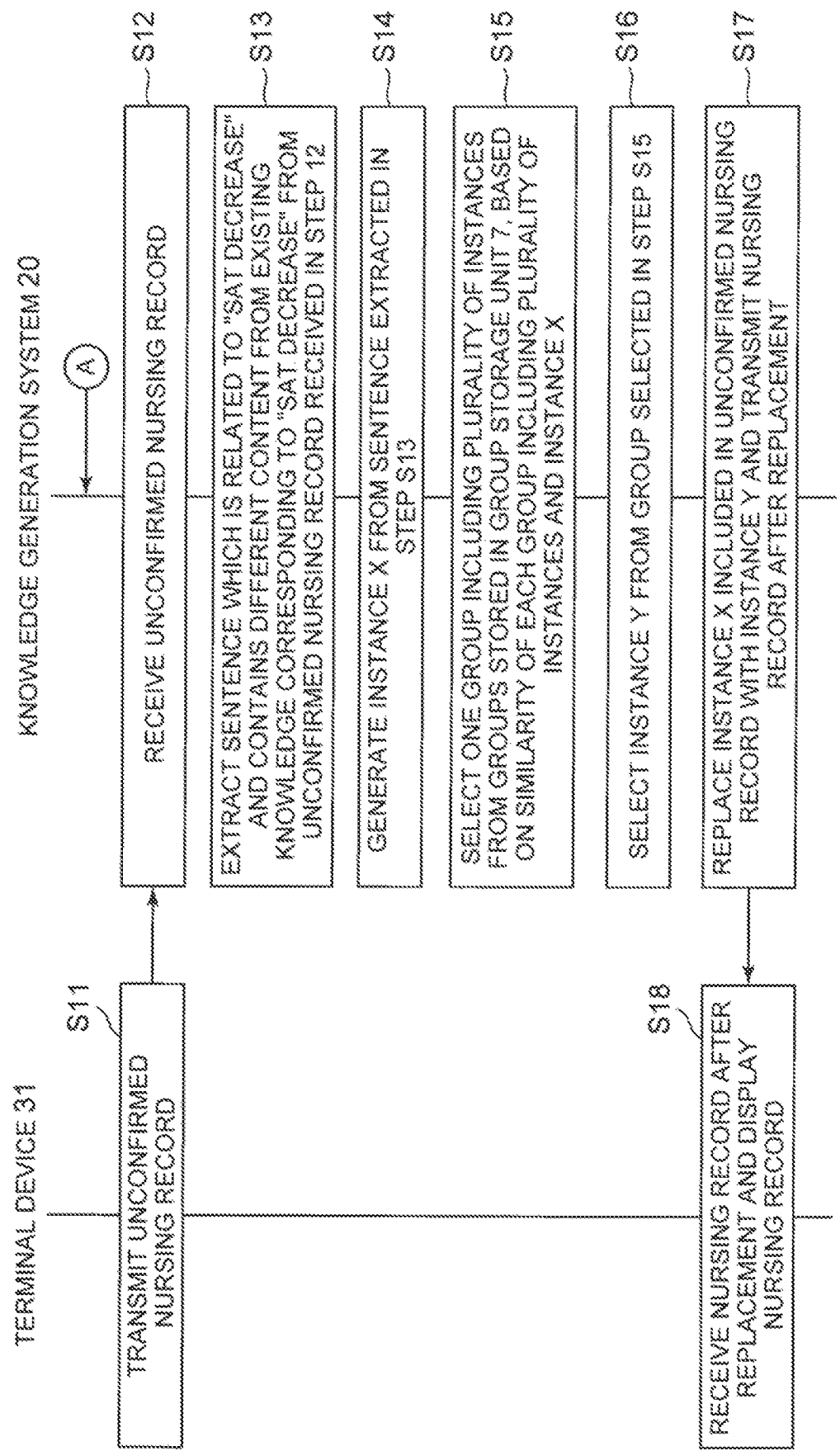
FIG. 12 It depicts a flowchart illustrating an example of a processing progress of knowledge generation processing.
Figure 13:
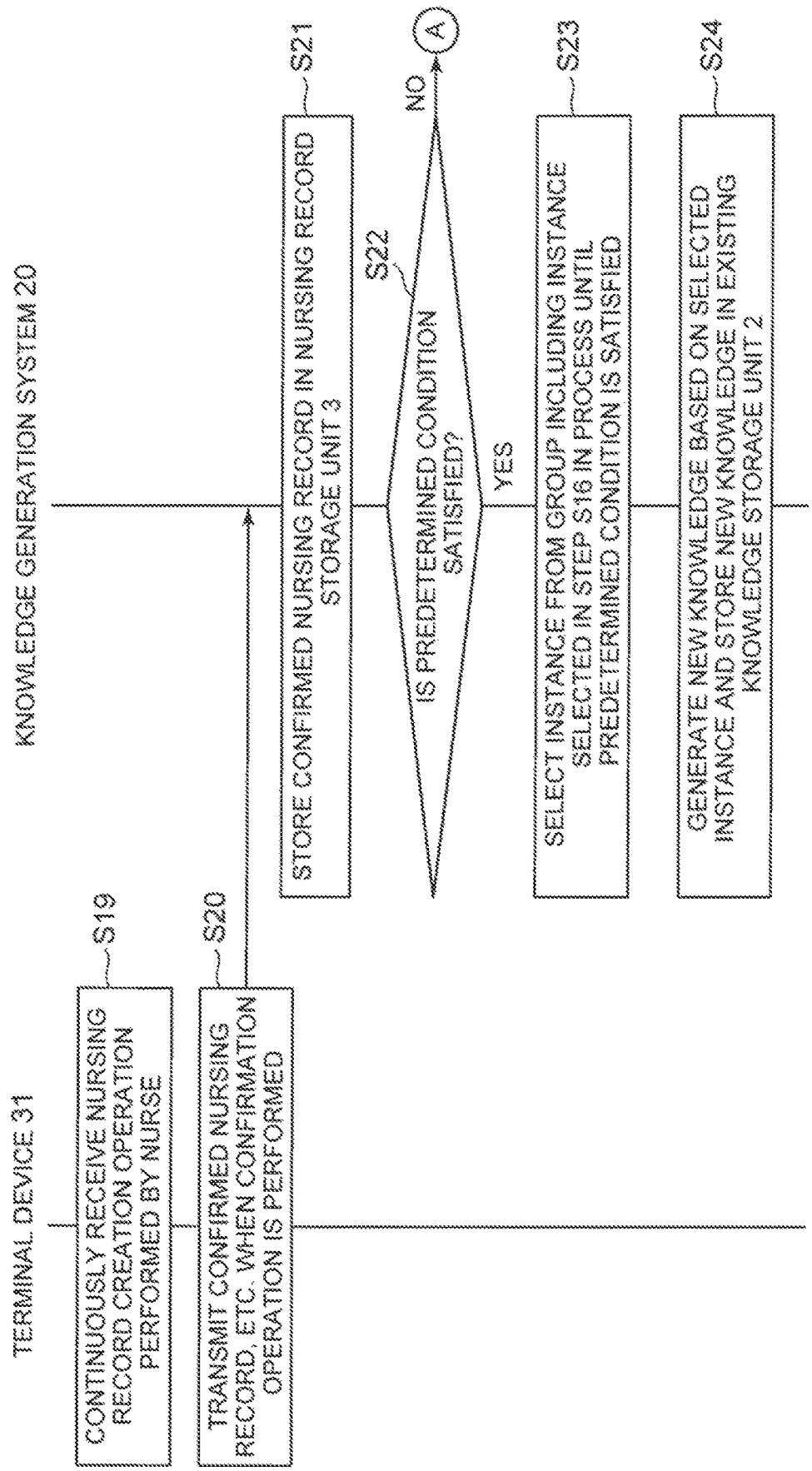
FIG. 13 It depicts a flowchart illustrating the example of the processing progress of the knowledge generation processing.

FIGS. 12 and 13 are flowcharts illustrating an example of a processing progress of knowledge generation processing. Note that details of the items that have been already described will be omitted.

A nurse creates a new nursing record by inputting a character string into the terminal device 31. It is assumed that a confirmation operation of the nursing record (for example, a click operation of the confirmation button 52 illustrated in FIG. 7 or the like) has not been performed yet.

The terminal device 31 transmits an unconfirmed nursing record to the knowledge generation system 20 (Step S11). The sentence extraction unit 9 of the knowledge generation system 20 receives the unconfirmed nursing record via the communication interface 8 (Step S12).

Then, the sentence extraction unit 9 extracts a sentence related to "SAT decrease" from the unconfirmed nursing record received in Step S12, the sentence including a different content from existing knowledge corresponding to "SAT decrease" (Step S13).

Next, the instance generation unit 10 generates an instance X by deleting a phrase representing "SAT decrease" from the sentence extracted in Step S13 (Step S14).

Next, the group selection unit 11 selects one group including a plurality of instances from the groups related to "SAT decrease" and stored in the group storage unit 7, based on a similarity between each of groups including a plurality of instances and the instance X generated in Step S14 (Step S15).

Next, the instance selection unit 12 selects an instance Y from the group selected in Step S15 (Step S16).

Next, the replacement unit 13 replaces the instance X included in the undetermined nursing record with the instance Y, and transmits the nursing record after replacement to the terminal device 31 (Step S17).

The terminal device 31 receives the nursing record after replacement transmitted in Step S17 and displays the nursing record on the display device (Step S18).

Then, the terminal device 31 continuously receives the operation of creating a nursing record performed by the nurse (Step S19). At this time, when determining that it is necessary to correct a character string corresponding to the instance Y included in the nursing record, the nurse corrects the character string and continues to create a nursing record. When determining that it is unnecessary to correct the character string corresponding to the instance Y, the nurse continues to create a nursing record without correcting the character string.

When an operation of confirming the nursing record (for example, a click operation of the confirmation button 52) is performed, the terminal device 31 transmits, to knowledge generation system 20, information indicating that the nursing record has been confirmed, the confirmed nursing record, and information indicating whether or not the character string replaced by the replacement unit 13 has been corrected by the nurse (Step S20).

The knowledge generation unit 14 of the knowledge generation system 20 receives each information transmitted in Step S20. Then, the knowledge generation unit 14 stores the confirmed nursing record in the nursing record storage unit 3 (Step S21).

Next, the knowledge generation unit 14 determines whether or not a predetermined condition is satisfied (Step S22). Since various examples of the predetermined conditions have already been described, the description thereof will be omitted here.

If the predetermined condition is not satisfied (No in Step S22), the knowledge generation system 20 waits until next unconfirmed nursing record is received from the terminal device 31, and repeats the processes in Step S12 and the subsequent steps when receiving the unconfirmed nursing record.

If the predetermined condition is satisfied (Yes in Step S22), the knowledge generation unit 14 selects an instance from a group including the instance selected in Step S16 in a process until the predetermined condition is satisfied (Step S23). An example of instance selection in Step S23 has been described in "Example 1" to "Example 5" described above, and thus, the description thereof will be omitted here.

Next, the knowledge generation unit 14 generates new knowledge based on the instance selected in Step S23, and stores the new knowledge in the existing knowledge storage unit 2 (Step S24).

According to the present exemplary embodiment, the replacement unit 13 transmits a nursing record in which the instance X has been replaced with the instance Y selected by the instance selection unit 12 to the terminal device 31, and the terminal device 31 displays the nursing record. Therefore, it can be said that the replacement unit 13 presents the instance Y to the nurse using the terminal device 31.

Then, it can be said that the fact that the predetermined condition is satisfied means that the nurse confirms the instance Y when creating the nursing record and determines that there is no problem in the instance Y.

The knowledge generation unit 14 selects an instance from a group including the instance Y determined as above, and generates knowledge based on the instance.

In addition, the nurse may create a nursing record as normal work in order to generate new knowledge. Then, when a character string in a nursing record being created is replaced at that time, the nurse may determine whether to correct the replaced character string (that is, the instance Y), continue to create a nursing record while correcting the nursing record depending on the determination, and perform the confirmation operation (for example, the click operation of the confirmation button 52) at the time when the nursing record is confirmed.

Therefore, knowledge can be newly generated in a process of performing normal work by the nurse according to the present exemplary embodiment. As a result, a new set of knowledge can be obtained.

In addition, the terminal device 31 accesses the knowledge generation system 20, retrieves knowledge stored in the existing knowledge storage unit 2 using an event specified by the nurse as a key, and displays the knowledge obtained as the search result in the present exemplary embodiment. Therefore, the nurse can browse the newly generated knowledge stored in the existing knowledge storage unit 2. Therefore, even a new nurse can appropriately perform patient assessment.

Next, a modification of the exemplary embodiment of the present invention will be described.

In Step S17, the replacement unit 13 may transmit information indicating the instance Y and the character string to be replaced (instance X) to the terminal device 31 before transmitting the nursing record after replacement. Then, for example, the terminal device 31 may display a balloon in which the instance Y is described near the character string corresponding to the instance X on the screen illustrated in FIG. 7. Then, the terminal device 31 receives an operation of whether or not to approve the replacement from the nurse, and returns information indicating whether or not to approve the replacement to the replacement unit 13. When receiving the information indicating the approval of the replacement, the replacement unit 13 may transmit the nursing record after the replacement (Step S17). When the replacement unit 13 receives information indicating that the replacement is not approved, the knowledge generation system 20 waits until next unconfirmed nursing record is received from the terminal device 31, and repeats the processes in Step S12 and the subsequent steps when receiving the unconfirmed nursing record.

In addition, the instance selection unit 12 may randomly select an instance from a group when selecting an instance from the group selected by the group selection unit 11 (Step S16). Similarly, the knowledge generation unit 14 may randomly select an instance from a group when selecting an instance from the group (Step S23).

In addition, the case where the knowledge generation system 20 is applied to the work of the nurse has been described as an example in the above description. As described above, the present invention is applicable to the work in which work record creation is included in a series of work. Therefore, the work to which the present invention is applied is not limited to the nurse work, and may be, for example, a manufacturing work, an inspection work, and the like in a factory or the like.

Figure 14:
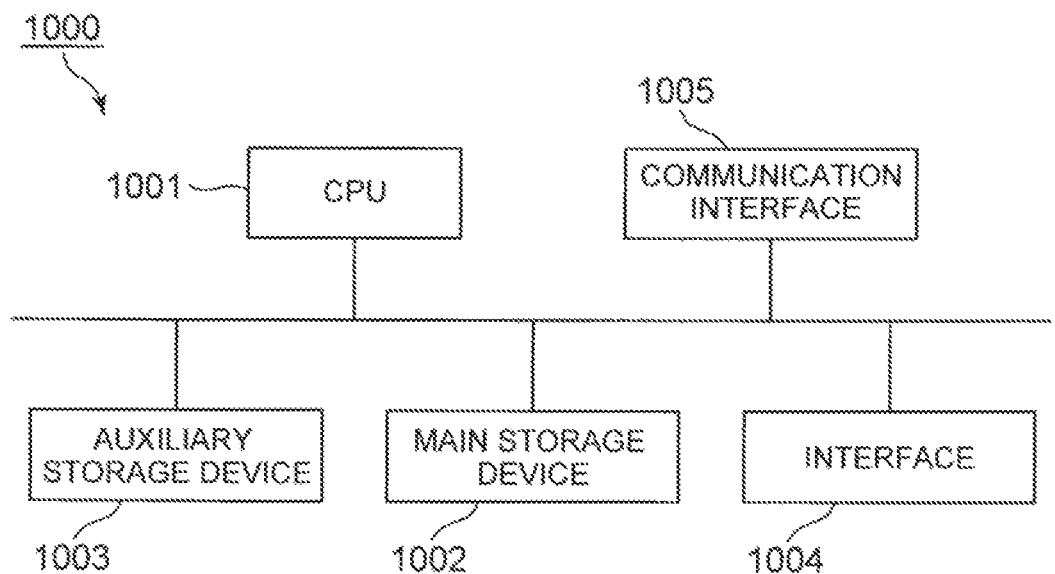
FIG. 14 It depicts a schematic block diagram illustrating a configuration example of a computer according to the knowledge generation system of the exemplary embodiment of the present invention.

FIG. 14 is a schematic block diagram illustrating a configuration example of a computer according to the knowledge generation system of the above exemplary embodiment. A computer 1000 includes a CPU 1001, a main storage device 1002, an auxiliary storage device 1003, an interface 1004, and a communication interface 1005.

The knowledge generation system in the present exemplary embodiment is implemented in the computer 1000, and its operation is stored in the auxiliary storage device 1003 in the form of a knowledge generation program. The CPU 1001 reads the knowledge generation program from the auxiliary storage device 1003 and develops the knowledge generation program on the main storage device 1002, and executes the operations described in the above exemplary embodiment and its modification according to the knowledge generation program.

The auxiliary storage device 1003 is an example of a non-transitory tangible medium. Other examples of the non-transitory tangible medium include a magnetic disk, a magneto-optical disk, a compact disk read-only memory (CD-ROM), a digital versatile disk read-only memory (DVD-ROM), a semiconductor memory, and the like connected via the interface 1004. In addition, when the program is distributed to the computer 1000 via a communication line, the computer 1000 may expand the program into the main storage device 1002 and execute the above-described processes in response to the distribution.

In addition, the program may be configured to implement some of the above-described processes. Further, the program may be a differential program which implements the above-described processes in combination with other programs that have been already stored in the auxiliary storage device 1003.

In addition, some or all of constituent elements may be implemented using a general-purpose or dedicated circuit (circuitry), a processor, or a combination thereof. These may be configured by a single chip, or may be configured by a plurality of chips connected via a bus. Some or all of constituent elements may be implemented using a combination of the above-described circuits and the like and a program.

When some or all of the respective constituent elements are realized by a plurality of information processing devices or circuits, the plurality of information processing devices or circuits may be intensively arranged or distributedly arranged. For example, the information processing devices, circuits, and the like may be implemented in the form of being connected via a communication network such as a client and server system and a cloud computing system.

Figure 15:
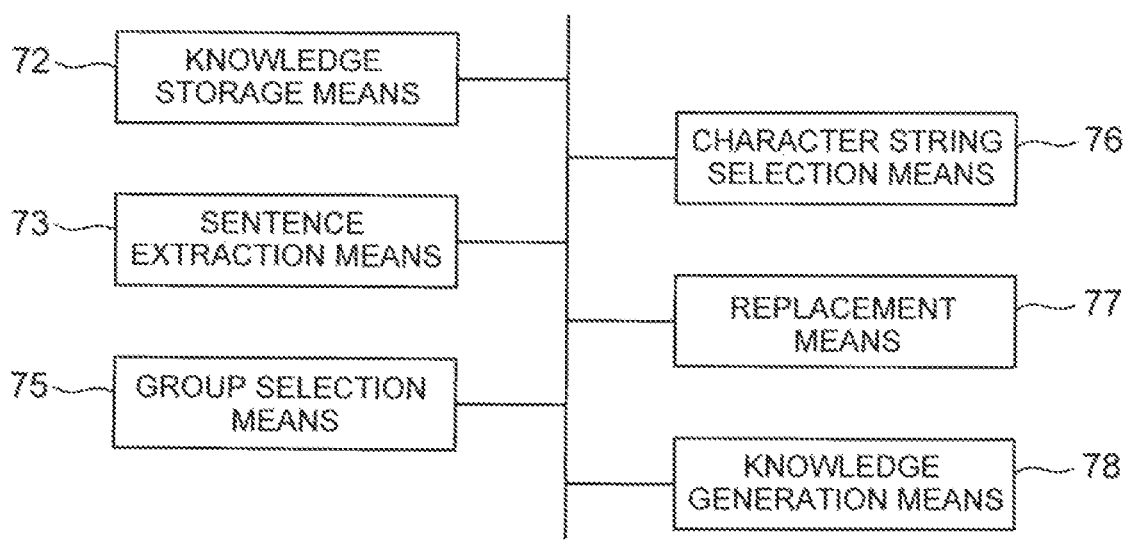
FIG. 15 It depicts a block diagram illustrating an outline of the knowledge generation system of the present invention.

Next, an outline of the present invention will be described. FIG. 15 is a block diagram illustrating an outline of the knowledge generation system of the present invention. The knowledge generation system of the present invention includes a knowledge storage means 72, a sentence extraction means 73, a group selection means 75, a character string selection means 76, a replacement means 77, and a knowledge generation means 78.

The knowledge storage means 72 (for example, existing knowledge storage unit 2) stores knowledge which is information representing a cause or coping method corresponding to an event.

The sentence extraction means 73 (for example, sentence extraction unit 9) extracts a sentence that is different from a cause or a coping method included in knowledge corresponding to a predetermined event and is related to the predetermined event, from an unconfirmed work record.

The group selection means 75 (for example, group selection unit 11) selects any one group including a plurality of character strings among groups of character strings, obtained by grouping the character strings which are likely to represent the cause or coping method corresponding to the event and are obtained from a past work record, based on a similarity between each of the groups including the plurality of character strings and a first character string (for example, the instance X) of the extracted sentence that is likely to represent the cause or coping method.

The character string selection means 76 (for example, instance selection unit 12) selects a character string included in the selected group as a second character string (for example, the instance Y).

The replacement means 77 (for example, replacement unit 13) replaces the first character string in the work record with the second character string selected by the character string selection means 76.

The knowledge generation means 78 (for example, knowledge generation unit 14) generates new knowledge based on any of the character strings included in the group when a predetermined condition regarding a confirmation status of the work record in which the first character string has been replaced with the second character string is satisfied.

According to such a configuration, the replacement means 77 replaces the first character string, included in the sentence extracted from the unconfirmed work record, with the second character string. Then, the knowledge generation means 78 generates knowledge according to the confirmation status of the work record whose replacement has been performed. Therefore, the knowledge can be newly generated in the process of performing the normal work by the worker.

The exemplary embodiment of the present invention described above may also be described as in the following supplementary notes, but is not limited to the following.

(Supplementary Note 1)

A knowledge generation system including:
a knowledge storage means for storing knowledge which is information representing a cause or coping method corresponding to an event;
a sentence extraction means for extracting a sentence which is different from a cause or a coping method included in knowledge corresponding to a predetermined event and is related to the predetermined event from an unconfirmed work record;
a group selection means for selecting any one group including a plurality of character strings among groups of character strings, obtained by grouping the character strings which are likely to represent the cause or coping method corresponding to the event and are obtained from a past work record, based on a similarity between each of the groups including the plurality of character strings and a first character string of the extracted sentence that is likely to represent the cause or coping method;
a character string selection means for selecting a character string included in the selected group including the plurality of character strings as a second character string;
a replacement means for replacing the first character string in the work record with the second character string selected by the character string selection means; and
a knowledge generation means for generating new knowledge based on any of the character strings included in the group when a predetermined condition regarding a confirmation status of the work record in which the first character string has been replaced with the second character string is satisfied.

(Supplementary Note 2)

The knowledge generation system according to Supplementary note 1, wherein
the group is obtained by grouping character strings based on vectors that represent the character strings.

(Supplementary Note 3)

The knowledge generation system according to Supplementary note 1 or 2, wherein
the group selection means selects the group using a distance between each of vectors representing centers of groups including a plurality of character strings and a vector representing the first character string, as a similarity between each of the groups and the first character string.

(Supplementary Note 4)

The knowledge generation system according to any one of Supplementary notes 1 to 3, wherein
the character string selection means selects the second character string from the selected group based on a distance between each of vectors representing character strings in the selected group and a vector representing the first character string.

(Supplementary Note 5)

The knowledge generation system according to any one of Supplementary notes 1 to 4, wherein
the character string selection means selects the second character string from the selected group while allowing the second character string selected once to be selected again.

(Supplementary Note 6)

The knowledge generation system according to any one of Supplementary notes 1 to 4, wherein
the character string selection means selects a second character string that is different from the second character string selected once when selecting the second character string from the group.

(Supplementary Note 7)

The knowledge generation system according to any one of Supplementary notes 1 to 5, wherein
the predetermined condition is a condition that an identical second character string is selected a plurality of times from an identical group by the character string selection means and the work record in which the first character string has been replaced with the second character string is confirmed a predetermined number of times without any correction to the second character string.

(Supplementary Note 8)

The knowledge generation system according to Supplementary note 7, wherein
the knowledge generation means generates new knowledge based on the second character string selected the plurality of times from the group when the predetermined condition is satisfied.

(Supplementary Note 9)

The knowledge generation system according to any one of Supplementary notes 1 to 5, wherein
the predetermined condition is a condition that a second character string is selected a plurality of times from an identical group by the character string selection means and the work record in which the first character string has been replaced with the selected second character string is confirmed a predetermined number of times without any correction to the selected second character string; and
the knowledge generation means generates new knowledge based on the second character string that has been most frequently selected by the character string selection means when the predetermined condition is satisfied.

(Supplementary Note 10)

The knowledge generation system according to any one of Supplementary notes 1 to 6, wherein
the predetermined condition is a condition that a second character string is selected a plurality of times from an identical group by the character string selection means, and
the work record in which the first character string has been replaced with the selected second character string is confirmed a predetermined number of times without any correction to the selected second character string.

(Supplementary Note 11)

The knowledge generation system according to Supplementary note 10, wherein
the knowledge generation means generates new knowledge based on a character string selected based on a length of each of the character strings included in the group when the predetermined condition is satisfied.

(Supplementary Note 12)

The knowledge generation system according to Supplementary note 10, wherein the knowledge generation means generates new knowledge based on a character string selected from a group using a distance between a vector representing a center of the group and each of vectors representing character strings included in the group when the predetermined condition is satisfied.

(Supplementary Note 13)

The knowledge generation system according to Supplementary note 10, wherein the knowledge generation means generates new knowledge based on a character string selected from a group using a distance between a vector representing a center of the group and each of vectors representing character strings included in the group, and a length of each of the character strings included in the group when the predetermined condition is satisfied.

(Supplementary Note 14)

The knowledge generation system according to any one of Supplementary notes 1 to 13, wherein the knowledge generation means generates a combination of each of words included in a character string selected from a group and a predetermined event as new knowledge.

(Supplementary Note 15)

The knowledge generation system according to any one of Supplementary notes 1 to 14, further including:

a pre-processing sentence extraction means for extracting a sentence related to a predetermined event from a work record created in past, the sentence containing a different content from existing knowledge corresponding to the predetermined event;

a character string generation means for generating character strings obtained by removing a phrase representing the predetermined event from the sentence extracted by the pre-processing sentence extraction means; and a grouping means for grouping the character strings generated by the character string generation means.

(Supplementary Note 16)

The knowledge generation system according to any one of Supplementary notes 1 to 15, wherein the knowledge generation system is applied to knowledge generation of nurse work.

(Supplementary Note 17)

A knowledge generation method for causing a computer including a knowledge storage means for storing knowledge which is information representing a cause or coping method corresponding to an event, to execute:

a sentence extraction process of extracting a sentence which is different from a cause or a coping method included in knowledge corresponding to a predetermined event and is related to the predetermined event from an unconfirmed work record;

a group selection process of selecting any one group including a plurality of character strings among groups of character strings, obtained by grouping the character strings which are likely to represent the cause or coping method corresponding to the event and are obtained from a past work record, based on a similarity between each of the groups including the plurality of character strings and a first character string of the extracted sentence that is likely to represent the cause or coping method;

a character string selection process of selecting a character string included in the selected group including the plurality of character strings as a second character string;

a replacement process of replacing the first character string in the work record with the second character string selected in the character string selection process; and a knowledge generation process of generating new knowledge based on any of the character strings included in the group when a predetermined condition regarding a confirmation status of the work record in which the first character string has been replaced with the second character string is satisfied.

(Supplementary Note 18)

A knowledge generation program, installed in a computer including a knowledge storage means for storing knowledge which is information representing a cause or coping method corresponding to an event, causing the computer to execute:

a sentence extraction process of extracting a sentence which is different from a cause or a coping method included in knowledge corresponding to a predetermined event and is related to the predetermined event from an unconfirmed work record;

a group selection process of selecting any one group including a plurality of character strings among groups of character strings, obtained by grouping the character strings which are likely to represent the cause or coping method corresponding to the event and are obtained from a past work record, based on a similarity between each of the groups including the plurality of character strings and a first character string of the extracted sentence that is likely to represent the cause or coping method;

a character string selection process of selecting a character string included in the selected group including the plurality of character strings as a second character string;

a replacement process of replacing the first character string in the work record with the second character string selected in the character string selection process; and a knowledge generation process of generating new knowledge based on any of the character strings included in the group when a predetermined condition regarding a confirmation status of the work record in which the first character string has been replaced with the second character string is satisfied.

The invention of the present application has been described above with reference to the exemplary embodiment, but the invention of the present application is not limited to the above-described exemplary embodiment. Various modifications that can be understood by the person skilled in the art can be made within a scope of the invention of the present application regarding the configuration and the details of the invention of the present application.

INDUSTRIAL APPLICABILITY

The present invention is suitably applied to generation of new knowledge related to work.

REFERENCE SIGNS LIST

1 Event storage unit
2 Existing knowledge storage unit
3 Work record storage unit 4 Pre-processing sentence extraction unit
5 Pre-processing instance generation unit
6 Grouping unit
7 Group storage unit
8 Communication interface
9 Sentence extraction unit
10 Instance generation unit
11 Group selection unit
12 Instance selection unit
13 Replacement unit
14 Knowledge generation unit
20 Knowledge generation system
31 Terminal device

What is claimed is:

1. A knowledge generation system comprising:
a storage device storing knowledge representing a cause or coping method corresponding to an event, the knowledge usable by workers in order to identify the cause or coping method corresponding to the event;
a processor; and
a memory storing instructions executable by the processor to, for each of a plurality of work records:
extract, from the work record, a sentence different from the cause or coping method included in the knowledge and corresponding to the event, the sentence related to the event;
obtain a plurality of groups of character strings from a past work record that are likely to represent the cause or coping method corresponding to the event, by:
for each character string, defining an n-dimensional vector having a plurality of elements respectively corresponding to a plurality of predetermined words, such that each element is set to a value of 1 when the character string includes the predetermined word corresponding to the element and is set to a value of 0 when the character string does not include the predetermined word corresponding to the element;
performing K-means clustering on the n-dimensional vector for each character string to generate a plurality of vector clusters corresponding to the plurality of groups of character strings, such that each character string belongs to the group corresponding to the vector cluster to which the n-dimensional vector for the character string has been cluster;
select, from among the plurality of groups of character strings, a group of character strings based on a similarity between each of the groups of character strings and a first character string of the extracted sentence that is likely to represent the cause or coping method, by:
defining an n-dimensional vector for the first character string having a plurality of elements respectively corresponding to the plurality of predetermined words, such that each element is set to a value of 1 when the first character string includes the predetermined word corresponding to the element and is set to a value of 0 when the first character string does not include the predetermined word corresponding to the element;
calculating a distance between the n-dimensional vector for the first character string and a center of each cluster;
selecting the group of character strings corresponding to the cluster for which the distance that has been calculated is smallest;
select a second character string from the selected group of character strings by:
calculating a distance between the n-dimensional vector for each character string in the selected group of character strings and the center of the cluster corresponding to the selected group of character strings;
selecting, as the second character string, the character string in the selected group of character strings for which the distance that has been calculated is smallest;
replace the first character string in the work record with the second character string; and
generate new knowledge based on a length of each of the character strings included in the selected group of character strings when a predetermined condition regarding a confirmation status of the work record in which the first character string has been replaced with the second character string is satisfied, wherein
the predetermined condition is that the second character string is selected a plurality of times from a same group of character strings and the work record in which the first character string has been replaced with the second character string is confirmed a predetermined number of times without any correction to the selected second character string, and
the knowledge is generated as work is performed and the work records are accordingly generated.

2. The knowledge generation system according to claim 1, wherein
the second character string, after having been selected from the selected group, is selectable again.

3. The knowledge generation system according to claim 1, wherein
after the second character string has been selected from the selected group, a different character string of the selected group is selected as the second character string.

4. The knowledge generation system according to claim 1, wherein
the new knowledge is generated as a combination of each of the character strings included in the selected group of character strings.

5. The knowledge generation system according to claim 1, wherein
the knowledge generation system is applied to knowledge generation of nurse work.

6. A knowledge generation method comprising:
storing, by a processor, knowledge representing a cause or coping method corresponding to an event, the knowledge usable by workers in order to identify the cause or coping method corresponding to the event;
extracting, by the processor and from the work record, a sentence different from the cause or coping method included in the knowledge and corresponding to the event, the sentence related to the event;
obtaining, by the processor, a plurality of groups of character strings from a past work record that are likely to represent the cause or coping method corresponding to the event, by:
for each character string, defining an n-dimensional vector having a plurality of elements respectively corresponding to a plurality of predetermined words, such that each element is set to a value of 1 when the character string includes the predetermined word corresponding to the element and is set to a value of 0 when the character string does not include the predetermined word corresponding to the element;
performing K-means clustering on the n-dimensional vector for each character string to generate a plurality of vector clusters corresponding to the plurality of groups of character strings, such that each character string belongs to the group corresponding to the vector cluster to which the n-dimensional vector for the character string has been cluster;

selecting, by the processor and from among the plurality of groups of character strings, a group of character strings, based on a similarity between each of the groups of character strings and a first character string of the extracted sentence that is likely to represent the cause or coping method, by:
defining an n-dimensional vector for the first character string having a plurality of elements respectively corresponding to the plurality of predetermined words, such that each element is set to a value of 1 when the first character string includes the predetermined word corresponding to the element and is set to a value of 0 when the first character string does not include the predetermined word corresponding to the element;
calculating a distance between the n-dimensional vector for the first character string and a center of each cluster;
selecting the group of character strings corresponding to the cluster for which the distance that has been calculated is smallest;

selecting, by the processor, a second character string from the selected group of character strings by:
calculating a distance between the n-dimensional vector for each character string in the selected group of character strings and the center of the cluster corresponding to the selected group of character strings;
selecting, as the second character string, the character string in the selected group of character strings for which the distance that has been calculated is smallest;

replacing, by the processor, the first character string in the work record with the second character string; and
generating, by the processor, new knowledge based on a length of each of the character strings included in the selected group of character strings when a predetermined condition regarding a confirmation status of the work record in which the first character string has been replaced with the second character string is satisfied, wherein
the predetermined condition is that the second character string is selected a plurality of times from a same group of character strings and the work record in which the first character string has been replaced with the second character string is confirmed a predetermined number of times without any correction to the selected second character string, and
the knowledge is generated as work is performed and the work records are accordingly generated.

7. A non-transitory computer-readable recording medium in which storing a knowledge generation program executable by a computer to perform:
storing knowledge representing a cause or coping method corresponding to an event, the knowledge usable by workers in order to identify the cause or coping method corresponding to the event;
extracting, from the work record, a sentence different from the cause or coping method included in the knowledge and corresponding to the event, the sentence related to the event;
obtaining a plurality of groups of character strings from a past work record that are likely to represent the cause or coping method corresponding to the event, by:
for each character string, defining an n-dimensional vector having a plurality of elements respectively corresponding to a plurality of predetermined words, such that each element is set to a value of 1 when the character string includes the predetermined word corresponding to the element and is set to a value of 0 when the character string does not include the predetermined word corresponding to the element;
performing K-means clustering on the n-dimensional vector for each character string to generate a plurality of vector clusters corresponding to the plurality of groups of character strings, such that each character string belongs to the group corresponding to the vector cluster to which the n-dimensional vector for the character string has been cluster;

selecting, from among the plurality of groups of character strings, a group of character strings, based on a similarity between each of the groups of character strings and a first character string of the extracted sentence that is likely to represent the cause or coping method, by:
defining an n-dimensional vector for the first character string having a plurality of elements respectively corresponding to the plurality of predetermined words, such that each element is set to a value of 1 when the first character string includes the predetermined word corresponding to the element and is set to a value of 0 when the first character string does not include the predetermined word corresponding to the element;
calculating a distance between the n-dimensional vector for the first character string and a center of each cluster;
selecting the group of character strings corresponding to the cluster for which the distance that has been calculated is smallest;

selecting a second character string from the selected group of character strings by:
calculating a distance between the n-dimensional vector for each character string in the selected group of character strings and the center of the cluster corresponding to the selected group of character strings;
selecting, as the second character string, the character string in the selected group of character strings for which the distance that has been calculated is smallest;

replacing the first character string in the work record with the second character string; and
generating new knowledge based on a length of each of the character strings included in the selected group of character strings when a predetermined condition regarding a confirmation status of the work record in which the first character string has been replaced with the second character string is satisfied, wherein
the predetermined condition is that the second character string is selected a plurality of times from a same group of character strings and the work record in which the first character string has been replaced with the second character string is confirmed a predetermined number of times without any correction to the selected second character string, and
the knowledge is generated as work is performed and the work records are accordingly generated.

* * * * *